US006355246B1

(12) United States Patent
Kruger et al.

(10) Patent No.: US 6,355,246 B1
(45) Date of Patent: Mar. 12, 2002

(54) FELINE CALICIVIRUS ISOLATED FROM CAT URINE AND VACCINES THEREOF

(75) Inventors: John M. Kruger; Roger K. Maes, both of Okemos; Aivars Vilnis, deceased, late of East Lansing, all of MI (US), by Maija Kalnberza, legal reprensentative

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/590,020

(22) Filed: Jun. 8, 2000

Related U.S. Application Data
(60) Provisional application No. 60/138,484, filed on Jun. 10, 1999.

(51) Int. Cl.[7] ................ A61K 39/12; A61K 39/00; A61K 39/02; A61K 39/125; C07K 1/00
(52) U.S. Cl. .................. 424/186.1; 424/184.1; 424/185.1; 424/186.1; 424/204.1; 424/235.1; 424/216.1; 424/530; 424/350; 424/514; 424/44
(58) Field of Search .................. 424/184.1, 185.1, 424/186.1, 204.1, 235.1, 216.1; 530/350; 514/44

(56) References Cited

U.S. PATENT DOCUMENTS

| | | |
|---|---|---|
| 3,937,812 A | 2/1976 | Bittle et al. |
| 3,944,469 A | 3/1976 | Bittle et al. |
| 4,486,530 A | 12/1984 | David et al. |
| 4,786,589 A | 11/1988 | Rounds et al. |
| 5,169,789 A | 12/1992 | Bernstein et al. |
| 5,229,293 A | 7/1993 | Matsuura et al. |
| 5,266,313 A | 11/1993 | Esposito et al. |
| 5,338,683 A | 8/1994 | Paoletti et al. |
| 5,494,807 A | 2/1996 | Paoletti et al. |
| 5,559,041 A | 9/1996 | Kang et al. |
| 5,561,064 A | 10/1996 | Marquet et al. |
| 5,580,859 A | 12/1996 | Felgner |
| 5,585,100 A | 12/1996 | Mond et al. |
| 5,589,384 A | 12/1996 | Liscombe |
| 5,589,466 A | 12/1996 | Felgner |
| 5,620,845 A | 4/1997 | Gould et al. |
| 5,656,448 A | 8/1997 | Kang et al. |
| 5,693,761 A | 12/1997 | Queen et al. |
| 5,693,762 A | 12/1997 | Queen et al. |
| 5,695,928 A | 12/1997 | Stewart et al. |
| 5,703,055 A | 12/1997 | Felgner |

(List continued on next page.)

FOREIGN PATENT DOCUMENTS

EP  0 484 382  3/1995

OTHER PUBLICATIONS

Clarke and Lambden in J. Gen. Virol. 78: 291–301 (1997).
Motin et al., Infect. Immun. 64: 4313–4318 (1996).
Yokoyama, N., et al., Vaccine, vol. 14, No. 17/18, pp. 1657–1663 (1996).

*Primary Examiner*—Hankyel T. Park
*Assistant Examiner*—Stacy S. Brown
(74) *Attorney, Agent, or Firm*—Ian C. McLeod

(57) ABSTRACT

The present invention provides an isolated feline calicivirus and mutants thereof, which were isolated from the urine of a cat with lower urinary tract disorder. The present invention further provides nucleic acid clones of the virus, in particular, a clone which encodes the capsid antigen of the virus. The present invention is useful for providing a live or killed virus vaccine comprising the virus or mutants thereof, a subunit vaccine comprising the capsid antigen of the virus, a nucleic acid vaccine encoding the capsid antigen of the virus, and a recombinant virus vector vaccine encoding the capsid antigen of the virus. The present invention also provides a method for isolating feline calicivirus from urine and an assay for diagnosing cats infected with feline calicivirus.

18 Claims, 1 Drawing Sheet

```
                                                      (A)                                       ↓
F9  PEFGTVWDCD  RSPLEIYLES  ILGDDEWAST  FDAVDPVVPP  MHWGAAGKIF  QPHPGVLMHH  LIGKVAAGWD  PDLPLIRLEA
UI  M        N Q                        Y I A       DD                      A    EA     F    G
                                                      (B)
F9  DDGSITAPEQ  GTMVGGVIAE  PSAQMSTAAD  MATGKSVDSE  WEAFFSFHTS  VNWSTSETQG  KILFKQSLGP  LLNPYLEHLA
UI             T                        A
                                                      (B)
F9  KLYVAWSGSI  EVRFSISGSG  VFGGKLAAIV  VPPGVDPVQS  TSMLQYPHVL  FDARQVEPVI  FCLPDLRSTL  YHLMSDTDTT
U1             V                        IE                                  AI    N
                                                      (B)
F9  SLVIMVYNDI  INPYANDANS  SGCIVTVETK  PGPDFKFHLL  KPPGSMLTHG  SIPSDLIPKT  SSLWIGNRYW  SDITDFVIRP
U1             L         T                                     V       S            H         I
                                   ↓(C)↓                (D)                        ↓     (E)
F9  FVFQANRHFD  FNQETAGWST  PRFRPISVTI  T EQNGA KLGI  GVATDYIVPG  IPDGWPDTTI  PGELIPAGDY AITNGTGNDI
U1                         TI V S S MS                                       EQ T     I  S  ASN T
                                                      (E)
F9  TTATGYDTAD IIKNNTNFRG MYICGSLQRA WGDKKISNTA  FITTATLDGD  NNNKINPCNT  IDQSKIVVFQ DNHVGKKAQT
U1  A     AE T VT    KS                          VRK N      SIEPS ---    MTKL  Y    EEV
                                                      (F)
F9  SDD TLALLGY TGIGEQAIGS DRDRVVRIST  LPETGARGGN  HPIFYKNSIK  LGYVIRSIDV  FNSQILHTSR QLSLNHYLLP
U1  I        E          K          V                                                          N
                                                      (F)
F9  PDSFAVYRII DSNGSWFDIG IDSDGFSFVG  VSGFGKLEFP  LSASYMGIQL  AKIRLASNIR  SPMTKL
U1             L                  T             NLP                    V    S
```

U.S. PATENT DOCUMENTS

| | | |
|---|---|---|
| 5,716,784 A | 2/1998 | DiCesare |
| 5,716,822 A | 2/1998 | Wardley |
| 5,718,901 A | 2/1998 | Wardley |
| 5,725,863 A | 3/1998 | Daniels et al. |
| 5,728,587 A | 3/1998 | Kang et al. |
| 5,800,821 A | 9/1998 | Acheson et al. |
| 5,977,322 A | 11/1999 | Marks et al. |
| 6,010,703 A | 1/2000 | Maes et al. |

```
F9  PEFGTVWDCD RSPLEIYLES ILGDDEWAST FDAVDPVVPP MHWGAAGKIF QPHPGVLMHH LIGKVAAGWD PDLPLIRLEA
U1             M          N Q                       Y I A     DD                  A  EA      F   G
                                            (A)
                                                                                   (B)
F9  DDGSITAPEQ GTMVGGVIAE PSAQMSTAAD MATGKSVDSE WEAFFSFHTS VNWSTSETQG KILFKQSLGP LLNPYLEHLA
U1        T                     A
F9  KLYVAWSGSI EVRFSISGSG VFGGKLAAIV VPPGVDPVQS TSMLQYPHVL FDARQVEPVI FCLPDLRSTL YHLMSDTDTT
U1           V                                    IE                             AI    N
                                                                                   (B)
F9  SLVIMVYNDI INPYANDANS SGCIVTVETK PGPDFKFHLL KPPGSMLTHG SIPSDLIPKT SSLWIGNRYW SDITDFVIRP
U1        L       T                              V    S                                  H    I
                        ▼(C)                                       (D)                        (E)
F9  FVFQANRHFD FNQETAGWST PRFRPISVTI TEQNGAKLGI GVATDYIVPG IPDGWPDTTI PGELIPAGDY AITNGTGNDI
U1                                   TI V S S MS                          EQ T   I  S  ASN T
                                                                                   (E)
F9  TTATGYDTAD IIKNNTNFRG MYICGSLQRA WGDKKISNTA FITTATLDGD NNNKINPCNT IDQSKIVVFQ DNHVGKKAQT
U1     A     AETVT    KS                       VRK N SIEPS ---        MTKL Y     EEV
                                                           (F)
F9  SDDTLALLGY TGIGEQAIGS DRDRVVRIST LPETGARGGN HPIFYKNSIK LGYVIRSIDV FNSQILHTSR QLSLNHYLLP
U1  I             E           K   V                                                      N
                                                           (F)
F9  PDSFAVYRII DSNGSWFDIG IDSDGFSFVG VSGFGKLEFP LSASYMGIQL AKIRLASNIR SPMTKL
U1       L                   T                 NLP                    V    S

FIG. 1
```

FELINE CALICIVIRUS ISOLATED FROM CAT URINE AND VACCINES THEREOF

CROSS-REFERENCE TO RELATED APPLICATION

The application claims the benefit of U.S. Provisional Patent Application Ser. No. 60/138,484, which was filed Jun. 10, 1999.

STATEMENT REGARDING FEDERALLY SPONSORED RESEARCH OR DEVELOPMENT

Not Applicable.

BACKGROUND OF THE INVENTION (1) Field of the Invention

The present invention relates to an isolated feline calicivirus and mutants thereof isolated from the urine of a cat with lower urinary tract disorder which is useful for providing a vaccine for immunizing a cat against feline calicivirus. The present invention also relates to a nucleic acid clone which encodes the capsid protein of the isolated feline calicivirus. The present invention further relates to a live or killed vaccine comprising the isolated feline calicivirus or mutants thereof, a subunit vaccine comprising the capsid antigen of the isolated feline calicivirus, a nucleic acid vaccine comprising a nucleic acid clone of the isolated feline calicivirus, and a recombinant virus vector vaccine comprising nucleic acid encoding the capsid antigen of the isolated feline calicivirus. The present invention also relates to a method for isolating feline calicivirus from urine and to assays for diagnosing cats infected with feline calicivirus.

(2) Description of Related Art

Feline calicivirus (FCV) is a small RNA virus that has been implicated in a variety of diseases in cats. The virus possesses a single-stranded RNA genome that is the plus-strand which is also polyadenylated. The molecular biology of caliciviruses is described in a review article by Clarke and Lambden in *J. Gen. Virol.* 78: 291–301 (1997).

FCV is generally known to cause disease characterized by conjunctivitis, rhinitis, tracheitis, pneumonia and by vesicularization/ulceration of the epithelium of the oral cavity and also by fever, anorexia, lethargy, stiff gait, and sometimes nasal and ocular discharge. Morbidity is high, mortality may reach 30%, and recovery is followed by a prolong carrier state. However, the type of disease symptoms caused by FCV depends on the strain of FCV involved, the severity of exposure, and the type of response to the FCV by the infected cat. Thus, some strains of FCV will produce little or no disease whereas other strains, such as various low virulence strains, produce no or only moderate pyrexia but may produce ulcers of the mouth and high virulence strains produce pyrexia, anorexia, depression, dypspnea, or polypnea and sometimes death, particularly, in neonatal cats. In addition to ulcers of the mouth, which may or may not occur, pneumonia may also be produced.

Disorders of the lower urinary tract of cats, characterized by hematuria, dysuria, pollakiuria, and periuria (urination in inappropriate locations), affect over half a million cats in the United States annually. As with all species, feline lower urinary tract disorders (LUTD) may result from diverse causes which may be single, multiple and interacting, or unrelated. Identified causes of feline LUTD include bacterial, fungal, and parasitic urinary tract infections; uroliths; bladder neoplasms; connective tissue strictures; lesions of the prostrate gland; and extraluminal masses of the urethra. The specific underlying cause or causes of clinical signs remain unknown in a large percentage of the naturally occurring cases of feline LUTD. In humans, hemorrhagic cystitis has been associated with a number of viral agents such as adenovirus, herpesvirus, polyomaviruses, influenza virus, and retroviruses. In cats, herpesviruses, retroviruses, and caliciviruses have at one time or another been implicated as potential causative agents in the etiopathogenesis of feline idiopathic LUTD.

Calicivirus was first implicated as a potential -causative agent in LUTDs over 30 years ago, when investigators at Cornell University isolated a calicivirus from urine obtained from a Manx cat with spontaneous urethral obstruction. Experimental induction of urethral obstruction in 80% of conventionally reared cats following urinary bladder, aerosol, or contact exposure with the Manx-isolated calicivirus directly supported the concept that calicivirus was an etiological agent for some forms of LUTD. Despite these encouraging results, the failure to re-isolate feline calicivirus from urine past the fourth day post-infection, the lack of significant serum-neutralizing antibody responses to the Manx-isolated virus, and isolation of a syncytium-forming virus from all obstructed experimental cats prompted investigators to hypothesize that feline calicivirus was not a primary causative agent of LUTD. Rather, it was hypothesized that feline calicivirus incited other latent viruses present in the urinary tract to induce urethral obstructions. The Manx-isolated calicivirus was not preserved and is no longer available, and investigators have not been successful in isolating another calicivirus from urine.

Since the discovery of FCV, FCV has been the object of numerous attempts to provide a vaccine which would protect cats against FCV infection. In U.S. Pat. Nos. 3,937,812 and 3,944,469 to Bittle et al. the development of the attenuated calicivirus F-9 vaccine strain is disclosed. The vaccine is useful for immunizing cats against respiratory infections caused by feline calicivirus. However, as shown in U.S. Pat. No. 4,522,810 to Pedersen, the F-9 vaccine strain does not protect cats against all field strains of FCV, in particular, field strain FCV-2280. Therefore, the Pedersen patent discloses FCV vaccines which consist of either live attenuated or killed FCV-2280. Pedersen does not disclose whether FCV-2280 can protect cats against a broad range of FCV field strains.

More recently, it has been observed that vaccines comprising FCV F-9 under certain field and experimental conditions can induce clinical signs of infection in vaccinated cats. To address this problem, U.S. Pat. Nos. 5,716,822 and 5,718,901 to Wardley disclose subunit vaccines consisting of the capsid polypeptide from FCV strain CFI/68 FIV. Also disclosed are transfected cells containing cDNA encoding the capsid polypeptide and recombinant baculovirus, feline herpesvirus, and vaccinia virus vectors containing the cDNA encoding the capsid polypeptide. Both the transfected cells and the baculovirus vector are used to produce the capsid polypeptide which is then used to make the subunit vaccine. The subunit vaccines avoid the problem of residual pathogenicity which may be present in live FCV vaccines. The scope of protection that was afforded by the subunit vaccine was not disclosed.

Despite the availability of vaccines for immunizing cats against FCV, none of the present vaccines have been shown to be completely protective against all strains and isolates of FCV. In some cats, some of the present vaccines may even cause disease. Furthermore, because the present vaccines consist of FCV derived from FCV isolated from cats with FCV-induced respiratory disease, the ability of the current vaccines to protect cats against FCV-induced LUTD may be ineffective. Therefore, there is a need for a vaccine that provides feline calicivirus particles or particular peptides for immunizing cats against FCV-induced LUTD.

SUMMARY OF THE INVENTION

The present invention provides isolated feline caliciviruses, FCV-U1 and FCV-U2 and mutants thereof, which were isolated from the urine of cats with lower urinary tract disorders. The present invention further provides nucleic acid clones of FCV-U1 and FCV-U2. In particular, the present invention provides a clone which encodes the capsid antigen of FCV-U1 or FCV-U2. The present invention is useful for providing a live or killed virus vaccine which comprises FCV-U1 or FCV-U2 or mutants thereof, a subunit vaccine which comprise the capsid antigen of FCV-U1 or FCV-U2 or immunogenic fragment thereof, a nucleic acid vaccine comprising a nucleic acid clone which encodes the capsid antigen of FCV-U1 or FCV-U2 or immunogenic fragment thereof, and a recombinant virus vector vaccine which comprises nucleic acid encoding the capsid antigen of FCV-U1 or FCV-U2 or immunogenic fragment thereof. The present invention also provides a method for isolating feline calicivirus from urine and an assay for diagnosing cats infected with feline calicivirus.

Thus, the present invention provides a vaccine for immunizing cats against feline calicivirus comprising FCV-U1 or FCV-U2 or mutants thereof, in an effective amount to produce an immune response, and a pharmaceutically acceptable carrier. Optionally, the vaccine can further include an adjuvant. The FCV-U1 or FCV-U2 or mutant thereof is provided as a live vaccine, preferably attenuated, or it can be provided as an inactivated vaccine. In either the live, attenuated, or inactivated embodiments of the vaccine, the FCV-U1 or FCV-U2 vaccine can further include at least one other feline calicivirus strain, preferably selected from the group consisting of FCV-F9, FCV-LLK, FCV-M8, FCV-255, and FCV-2280, in addition to the FCV-U1 or FCV-U2 or mutant thereof.

The present invention also provides a vaccine for immunizing cats against feline calicivirus comprising a recombinant virus vector comprising a nucleotide sequence encoding the capsid antigen or immunogenic fragment thereof selected from the group consisting of FCV-U1, FCV-U2 or both, wherein the nucleic acid sequence is operably linked to a heterologous promoter sequence, in an effective amount to produce an immune response, and a pharmaceutically acceptable carrier. In particular, a vaccine as provided wherein the recombinant virus vector is selected from the group consisting of feline herpesvirus, raccoon poxvirus, canary poxvirus, adenovirus, Simliki forest virus, sindbis virus, and vaccinia virus. In a preferred embodiment, the nucleotide sequence encoding the capsid antigen or immunogenic fragment thereof comprises the amino acid sequence selected from the group consisting of SEQ ID NO:2, SEQ ID NO:4, and SEQ ID NO:6 or the nucleotide sequence encoding the capsid antigen or immunogenic fragment thereof comprises the nucleotide sequence selected from the group consisting of SEQ ID NO:1, SEQ ID NO:3, and SEQ ID NO:5.

Further still, the present invention provides a vaccine to immunize cats against feline calicivirus which comprises a nucleotide sequence or portion thereof encoding the capsid antigen or immunogenic fragment thereof of the calicivirus selected from the group consisting of FCV-U1, FCV-U2, or both, wherein the nucleic acid sequence is operably linked to a heterologous promoter sequence, in an effective amount to produce an immune response, and a pharmaceutically acceptable carrier. Preferably, the nucleotide sequence encoding the capsid antigen or immunogenic fragment thereof is in a plasmid, and in particular, the capsid antigen or immunogenic fragment thereof encoded by the nucleotide sequence comprises the amino acid sequence selected from the group consisting of SEQ ID NO:2, SEQ ID NO:4, or SEQ ID NO:6 or the capsid antigen is encoded by the nucleotide sequence selected from the group consisting of SEQ ID NO:1, SEQ ID NO:3, and SEQ ID NO:5.

Further still, the present invention provides a vaccine to immunize cats against feline calicivirus comprising an isolated capsid antigen or portion thereof selected from the group consisting of FCV-U1, FCV-U2, and both, in an effective amount to produce an immune response, and a pharmaceutically acceptable carrier. Preferably, the capsid antigen comprises the amino acid sequence selected from the group consisting of SEQ ID NO:2, SEQ ID NO:4, and SEQ ID NO:6.

The present invention also provides a method for immunizing a cat against feline calicivirus comprising administering to the cat an effective dose of a vaccine selected from the group consisting of a live FCV-U1 or mutant thereof, a killed FCV-U1 or mutant thereof, a recombinant virus vector comprising a nucleotide sequence encoding a capsid antigen or immunogenic fragment thereof of FCV-U1 or mutant thereof, a nucleotide molecule comprising a nucleotide sequence encoding the capsid antigen or immunogenic fragment thereof of FCV-U1 or mutant thereof, and an isolated capsid antigen or immunogenic fragment thereof of FCV-U1 or mutant thereof, in a pharmaceutically acceptable carrier. Preferably, the capsid antigen or immunogenic fragment thereof comprises the amino acid sequence selected from the group consisting of SEQ ID NO:2, SEQ ID NO:4, and SEQ ID NO:6 or the capsid antigen or immunogenic fragment thereof is encoded by the nucleotide sequence selected from the group consisting of SEQ ID NO:1, SEQ ID NO:3, and SEQ ID NO:5.

Further still, the present invention provides a method for immunizing a cat against feline calicivirus comprising administering to the cat an effective dose of a vaccine selected from the group consisting of a live FCV-U2 or mutant thereof, a killed FCV-U2 or mutant thereof, a recombinant virus vector comprising a nucleotide sequence encoding a capsid antigen or immunogenic fragment thereof of FCV-U2 or mutant thereof, a nucleotide molecule comprising a nucleotide sequence encoding the capsid antigen or immunogenic fragment thereof of FCV-U2 or mutant thereof, and an isolated capsid antigen or immunogenic fragment thereof of FCV-U2 or mutant thereof, in a pharmaceutically acceptable carrier.

The present invention also provides an isolated and purified culture of feline calicivirus FCV-U1 or mutant thereof deposited as ATCC PTA-3444 or an isolated and purified culture of feline calicivirus FCV-U2 or mutant thereof deposited as ATCC PTA-3445.

The present invention also provides a pure and isolated capsid antigen or immunogenic fragment thereof of feline calicivirus comprising the amino acid sequence selected from the group consisting of SEQ ID NO:2, SEQ ID NO:4, and SEQ ID NO:6. In particular, the pure and isolated capsid antigen or immunogenic fragment thereof, wherein the amino acid sequence is encoded by the nucleotide sequence selected from the group consisting of SEQ ID NO:1, SEQ ID NO:3, and SEQ ID NO:5.

Finally, the present invention provides a nucleotide molecule encoding a feline calicivirus capsid antigen or immunogenic fragment thereof comprising the nucleotide sequence selected from the group consisting of SEQ ID NO:1, SEQ ID NO:3, and SEQ ID NO:5.

Objects

Therefore, an object of the present invention is to provide a vaccine that immunizes cats against disease caused by feline calicivirus.

These and other objects of the present invention will become increasingly apparent with reference to the following drawings and preferred embodiments.

DESCRIPTION OF THE DRAWINGS

FIG. 1 is a comparative analysis of the capsid antigen amino acid sequences of the F-9 vaccine strain and the FCV-U1 isolated from urine. Differences in amino acid identity for the FCV-U1 strain (SEQ ID NO:4) are listed below the corresponding F-9 strain amino acid (SEQ ID NO:7). Arrows and bold letters in parentheses identify the six regions of the capsid antigen. Regions C and E, which correspond to the hypervariable region, are shaded.

DETAILED DESCRIPTION OF THE INVENTION

All patents, patent applications, government publications, government regulations, and literature references cited. in this specification are hereby incorporated herein by reference in their entirety. In case of conflict, the present description, including definitions, will control.

The following definitions are provided herein to promote a better understanding of the present invention.

The term "calicivirus capsid antigen" refers to the capsid antigen encoded by the FCV-U1 or FCV-U2 isolate or mutant thereof. For example, the capsid antigen encoded by the nucleotide sequence selected from the group consisting of SEQ ID NO:1, SEQ ID NO:3, and SEQ ID NO:5 or the capsid antigen which has the amino acid sequence shown in SEQ ID NO:2, SEQ ID NO:4, or SEQ ID NO:6.

The term "antigen" refers to an immunogenic polypeptide or fragment thereof which stimulates production of antibody or sensitized cells during an immune response. The term "antigen" further includes the whole pathogen, a particular polypeptide of the pathogen, or a fragment of the particular polypeptide. An antigen consists of multiple epitopes, each epitope of which is capable of causing the production of an antibody against the particular epitope.

The term "epitope" refers to an immunogenic region of an antigen which is recognized by a particular antibody molecule. In general, an antigen will possess one or more epitopes, each capable of binding an antibody that recognizes the particular epitope. An antibody can recognize a contiguous epitope which is an epitope that is a linear sequence of amino acids in the antigen molecule, or a non-contiguous epitope which is an epitope that spans non-contiguous amino acids in the antigen which have been brought together because of the three-dimensional structure of the antigen.

The term "antibody" refers to an immunoglobulin molecule with the capacity to bind with a specific antigen as the result of a specific immune response. Immunoglobulins are serum proteins made up of light and heavy polypeptide chains and divisible into classes, which contain within them antibody activities toward a wide range of antigens.

The term "polyclonal antibody" refers to a mixed population of antibodies made against a particular pathogen or antigen. In general, the population contains a variety of antibody groups, each group directed towards a particular epitope of the pathogen or antigen. To make polyclonal antibodies, the whole pathogen or an isolated antigen is introduced by inoculation or infection into a host which induced the host to make antibodies against the pathogen or antigen.

The term "monoclonal antibody" refers to antibodies produced by a single line of hybridoma cells all directed towards one epitope on a particular antigen. The antigen used to make the monoclonal antibody can be provided as an isolated protein of the pathogen or the whole pathogen. A hybridoma is a clonal cell line that consists of hybrid cells formed by the fusion of a myeloma cell and a specific antibody-forming cell. In general, monoclonal antibodies are of mouse origin; however, monoclonal antibody also refers to a clonal population of an antibody made against a particular epitope of an antigen produced by phage display technology or method that is equivalent to phage display or hybrid cells of non-mouse origin.

The term "active immunity" includes both humoral immunity and/or cell mediated immunity against feline calicivirus induced by vaccinating a cat with the vaccine of the present invention.

The term "passive immunity" refers to the protection against feline calicivirus provided to a cat as a result of vaccinating the cat with a vaccine comprising antibodies against the FCV-U1 or FCV-U2 feline calicivirus or mutant thereof or immunogenic fragment thereof.

Questions concerning the causative role of feline calicivirus in LUTD were compounded by the inability of other investigators to isolate feline calicivirus from urine obtained from cats with spontaneous forms of LUTD. However, previous studies investigating the role of viruses in natural feline LUTDs have depended upon conventional virus isolation techniques. As with all virus isolation techniques, isolation of feline calicivirus requires the live virus in specimens and absence of substances that are toxic to cell culture or inhibit virus replication. Feline calicivirus is extremely sensitive to the effects of urine, storage temperature, and freeze-thaw cycles. For example, freeze-thaw decreases the titer by about 1 log in serum-free medium and about 2–4 logs in urine. Survival of feline calicivirus in serum-free medium at 4° C. causes little change in virus titer after about 96 hours but in urine at 4° C., the titer decreased by 1 log after 48 hours and no virus survived beyond 72–96 hours. Survival of feline calicivirus at 37° C. in serum-free medium was between about 12 to 24 hours whereas survival in urine at 37° C. was less than 12 hours. Compounding the problem, feline urine appears to be highly toxic to standard cell-lines used for feline virus isolation. Consequently, the inability of other researchers to detect live viruses, particularly feline calicivirus, in the urine of cats with naturally occurring LUTD must be viewed with caution because negative findings by various investigators appear to be confounded by improper selection of naturally occurring cases of LUTD, insensitive or inappropriate virus detection methods, the virucidal nature of feline urine, and/or improper handling of samples.

Recent electron-microscope studies have identified calicivirus-like particles in the matrix of 38% of 92 urethral plugs obtained from male cats with obstructive idiopathic LUTD. Since urethral plug formation is a potential complication of idiopathic LUTD, detection of calicivirus-like particles in a substantial number of urethral plugs led to a re-examination of the hypothesis that feline calicivirus may have a role in idiopathic LUTD. As part of a prospective study using contemporary molecular biological methods in conjunction with conventional virus isolation techniques to investigate the prevalence of feline calicivirus urinary tract infections, a method was developed which enabled the present feline calicivirus isolates, FCV-U1 and FCV-U2, to be isolated from urine obtained from a nonobstructed cat with naturally occurring idiopathic LUTD. These isolates which were isolated from a cat with idiopathic LUTD indicate that calicivirus may be causally related to at least some idiopathic cases of LUTD.

To determine whether the FCV-U1 and FCV-U2 isolates were related to the F-9 feline calicivirus vaccine strain, the amino acid sequence of the gene encoding the capsid antigen of the isolates was compared to the amino acid sequence of the F-9 capsid antigen. Thus, viral RNA was extracted from FCV-U1 and reverse transcribed into cDNA using capsid antigen specific nucleotide primers. The cDNA was PCR amplified, cloned into a plasmid vector, propagated, and the cloned cDNA isolated by methods well known in the art. The cDNAs from 3 separate clones of the cloned cDNA were each bidirectionally sequenced on an automated fluorescent DNA sequencer. The 1882 bp nucleotide sequence of the capsid antigen of FCV-U1 for clones 3, 4, and 7 are shown in SEQ ID NO:1, SEQ ID NO:3, and SEQ ID NO:5, respectively, and the predicted amino acid sequence of the capsid antigen for each clone is shown in SEQ ID NO:2, SEQ ID NO:4, and SEQ ID NO:6, respectively. The 624 amino acid FCV-U2 capsid antigen shown in SEQ ID NO:4 (clone 4) was compared to the capsid antigen of the F-9 vaccine strain of feline calicivirus (SEQ ID NO:7), the results of which are shown in FIG. 1. Overall, the amino acid sequence has 86.7% identity to the capsid antigen of the F-9 vaccine strain. However, the amino acid sequences for hypervariable regions C and E of the FCV-U1 capsid antigen has only 40% and 63.1%, respectively, identity to the corresponding regions of the F-9 strain. Identity between the amino acid sequences of FCV-U1 capsid antigen regions A, B, D, and F are 85.3%, 92.8%, 100%, and 92.3%, respectively. The sequence comparisons indicate that the capsid antigen of FCV-U1 is genetically distinct and distinguishable from that of the F-9 vaccine strain. Thus, the present invention provides a feline calicivirus strain FCV-U1 that encodes a capsid antigen having the amino acid sequence selected from the group consisting of SEQ ID NO:2, SEQ ID NO:4, and SEQ ID NO:6, which is encoded by the nucleotide sequence of SEQ ID NO:1, SEQ ID NO:3, and SEQ ID NO:5, respectively. FCV-U1 and FCV-U2 were deposited at the Animal Health and Diagnostic Laboratory, Veterinary Medical Center, Michigan State University, East Lansing, Mich., 48824. In addition, FCV-U1 and FCV-U2 are deposited under the terms of the Budapest Treaty at the American Type Culture Collection (ATCC), 10801 University Boulevard, Manassas, Va. 20110-2209 on Jun. 8, 2001 as ATCC PTA-3444 and ATCC PTA-3445, respectively.

The FCV-U1 and FCV-U2 isolates and mutants thereof are useful for providing vaccines for immunizing cats against disease caused by feline calicivirus, in particular LUTD caused by particular feline calicivirus strains. Therefore, the present invention provides vaccines which are based upon live or killed FCV-U1 and FCV-U2 or mutants thereof, and upon particular immunogenic fragments thereof. The vaccine of the present invention is generally intended to be a prophylactic treatment which immunizes cats against disease caused by virulent strains of feline calicivirus. However, the vaccine is also intended for the therapeutic treatment of cats already infected with a virulent strain of feline calicivirus. For example, a vaccine comprising antibodies produced by immunizing a heterologous host with FCV-U1 or FCV-U2 or mutant thereof, or immunogenic fragment thereof, is used for the therapeutic treatment of a feline calicivirus-infected cat. However, even vaccines which provide active immunity, i.e., vaccines comprising FCV-U1 and FCV-U2 or mutants thereof, or immunogenic fragments thereof, have been shown in certain cases to be effective when given as a therapeutic treatment against various diseases. Thus, the immunity that is provided by the present invention can be either active immunity or passive immunity and the intended use of the vaccine can be either prophylactic or therapeutic.

The route of administration for any one of the embodiments of the vaccine of the present invention includes, but is not limited to, oronasal, intramuscular, intraperitoneal, intradermal, subcutaneous, intravenous, intraarterial, intraocular, and oral as well as transdermal or by inhalation or suppository. The preferred routes of administration include oronasal, intramuscular, intraperitoneal, intradermal, and subcutaneous injection. The vaccine can be administered by any means which includes, but is not limited to, syringes, nebulizers, misters, needleless injection devices, or microprojectile bombardment gene guns (Biolistic bombardment).

The vaccine for any one of the embodiments of the present invention is formulated in a pharmaceutically accepted carrier according to the mode of administration to be used. One skilled in the art can readily formulate a vaccine that comprises a live or killed FCV-U1 or FCV-U2 or mutant thereof, the FCV-U1 or FCV-U2 capsid antigen or immunogenic fragment thereof, a recombinant virus vector encoding the FCV-U1 or FCV-U2 capsid antigen or immunogenic fragment thereof, or a DNA molecule encoding the FCV-U1 or FCV-U2 capsid antigen or immunogenic fragment thereof. In cases where intramuscular injection is preferred, an isotonic formulation is preferred. Generally, additives for isotonicity can include sodium chloride, dextrose, mannitol, sorbitol, and lactose. In particular cases, isotonic solutions such as phosphate buffered saline are preferred. The formulations can further provide stabilizers such as gelatin and albumin. In some embodiments, a vaso-constrictive agent is added to the formulation. The pharmaceutical preparations according to the present invention are provided sterile and pyrogen free. However, it is well known by those skilled in the art that the preferred formulations for the pharmaceutically accepted carrier which comprise the vaccines of the present invention are those pharmaceutical carriers approved in the regulations promulgated by the United States Department of Agriculture, or equivalent government agency in a foreign country such as Canada or Mexico or any one of the European nations, for live feline calicivirus vaccines, killed feline calicivirus vaccines, polypeptide (antigen) subunit vaccines, recombinant virus vector vaccines, antibody vaccines, and DNA vaccines. Therefore, the pharmaceutically accepted carrier for commercial production of the vaccine of the present invention is a carrier that is already approved or will be approved by the appropriate government agency in the United States of America or foreign country. The vaccine can further be mixed with an adjuvant which is pharmaceutically acceptable. In certain formulations of the vaccine of the present invention, the vaccine is combined with other feline vaccines to produce a polyvalent vaccine product that can protect cats against a wide variety of diseases caused by other feline pathogens. Currently, polyvalent vaccine products are preferred by commercial manufacturers of feline vaccines. Therefore, in a preferred embodiment, the present invention provides a polyvalent vaccine which immunizes cats against feline calicivirus and at least one other feline pathogen, preferably selected from the group consisting of feline herpesvirus, feline leukemia virus, feline immunodeficiency virus, feline Chlamydia, and feline panleukopenia virus.

Inoculation of a cat is preferably by a single vaccination which produces a full, broad immunogenic response. In another embodiment of the present invention, the cat is subjected to a series of vaccinations to produce a full, broad immune response. When the vaccinations are provided in a series, the vaccinations can be provided between about one day apart to two weeks or longer between vaccinations. In particular embodiments, the cat is vaccinated at different sites simultaneously.

In one embodiment of the vaccine of the present invention, the vaccine comprises a live vaccine comprising FCV-U1 or FCV-U2 or mutant thereof. It is well known in the art that a calicivirus strain which is virulent when administered to a cat by the oronasal route, the natural route of infection, is generally apathogenic when administered by another route such as the intraperitoneal, intramuscular, intradermal, or subcutaneous routes. However, in certain cats, e.g., immunocompromised cats, inoculated by these other routes, the virus is causes disease. Therefore, it is desirable that particular live vaccines comprise an attenuated or mutated variant of FCV-U1 or FCV-U2, which stimulates the cat's immune system without causing disease. Methods for making attenuated viruses are well known in the art and include such methods as serial passage in cell culture on a suitable cell line or chemical mutagenesis. For example, attenuated variants of FCV-U1 or FCV-U2 are made by serial passage of the virus on a cell line such as Crandall-Reese Feline Kidney (CRFK) cells for between about 10 and 100 passages. During passage on the cell line, the virus loses its ability to cause disease in the cat, e.g., becomes apathogenic or non-pathogenic, while maintaining its ability to replicate in the cat and produce a protective immune response.

Therefore, to make the vaccine, feline calicivirus isolate, FCV-U1 or FCV-U2, or an attenuated or mutated variant thereof, is grown in cell culture on a suitable feline cell line, i.e., CRFK cells, to titers sufficient for producing a vaccine. The calicivirus is harvested according to methods well known in the art. The calicivirus is then concentrated, frozen, and stored at −70° C. or freeze-dried and stored at 4° C. The calicivirus prior to vaccination is mixed to an appropriate dosage, which is from about $10^3$ to $10^8$ tissue culture infectious doses per ml ($TCID_{50/ml}$) with a pharmaceutically acceptable carrier, such as a saline solution and/or an adjuvant, such as aluminum hydroxide. The live vaccine can further include, in addition to the FCV-U1 and/or FCV-U2 or mutant thereof, at least one feline calicivirus strain, preferably selected from the group consisting of FCV-F9, FCV-LLK, FCV-M8, FCV-255, and FCV-2280. In a preferred embodiment, the vaccine further includes a vaccine for immunizing a cat against at least one other feline pathogen, preferably selected from the group consisting of feline herpesvirus, feline leukemia virus, feline immunodeficiency virus, feline Chlamydia, and feline panleukopenia virus.

In another embodiment of the present invention, the vaccine comprises an inactivated or killed vaccine comprising FCV-U1 or FCV-U2 or mutant thereof. The inactivated vaccine is made by methods well known in the art. For example, once the virus is propagated to high titers, it would be readily apparent by those skilled in the art that the virus antigenic mass could be obtained by methods well known in the art. For example, the virus antigenic mass may be obtained by dilution, concentration, or extraction. All of these methods have been employed to obtain appropriate viral antigenic mass to produce vaccines. The calicivirus is inactivated by treatment with formalin or with binary ethyleneimine (BEI), both methods are well known to those skilled in the art.

Inactivation by formalin is performed by mixing the calicivirus suspension with 37% formaldehyde to a final formaldehyde concentration of 0.05%. The calicivirus-formaldehyde mixture is mixed by constant stirring for approximately 24 hours at room temperature. The inactivated calicivirus mixture is then tested for residual live virus by assaying for growth on a suitable feline cell line such as CRFK cells.

Inactivation by BEI is performed by mixing the calicivirus suspension of the present invention with 0.1 M BEI (2-bromo-ethylamine in 0.175 N NaOH) to a final BEI concentration of 1 mM. The calicivirus-BEI mixture is mixed by constant stirring for approximately 48 hours at room temperature, followed by the addition of 1.0 M sodium thiosulfate to a final concentration of 0.1 mM. Mixing is continued for an additional two hours. The inactivated calicivirus mixture is tested for residual live calicivirus by assaying for growth on a suitable feline cell line such as CRFK cells. The aforementioned inactivated calicivirus of the present invention is mixed with any one of the pharmaceutically acceptable adjuvants or physiological carriers for formulating inactivated virus vaccines to the appropriate dosage level. The inactivated vaccine further can include, in addition to FCV-U1 and/or FCV-U2 or mutant thereof, at least one feline calicivirus strain, preferably selected from the group consisting of FCV-F9, FCV-LLK, FCV-M8, FCV-255, and FCV-2280. In a preferred embodiment, the vaccine further includes a vaccine for immunizing a cat against at least one other feline pathogen, preferably selected from the group consisting of feline herpesvirus, feline leukemia virus, feline immunodeficiency virus, feline Chlamydia, and feline panleukopenia virus.

In a further embodiment of the present invention, the vaccine comprises a recombinant virus vector containing a nucleic acid encoding the capsid antigen of FCV-U1 or FCV-U2 or mutant thereof, or immunogenic fragment thereof, comprising the amino acid sequence selected from the group consisting of SEQ ID NO:2, SEQ ID NO: 4, and SEQ ID NO: 6, or comprising the nucleotide sequence selected from the group consisting of SEQ ID NO:1, SEQ ID NO:3, and SEQ ID NO:5. In one particular embodiment, the recombinant virus vector is a feline herpesvirus which immunizes a cat against both feline calicivirus and feline herpesvirus. In another embodiment, the recombinant virus vector comprises at least one other antigen, preferably selected from the group consisting of feline herpesvirus, feline leukemia virus, feline immunodeficiency virus, feline Chlamydia, and feline panleukopenia virus.

To make a recombinant virus vector that expresses the FCV-U1 or FCV-U2 capsid antigen or immunogenic fragment thereof, a cDNA encoding the capsid antigen or immunogenic fragment thereof is inserted into the genome of a virus vector such as herpesvirus, poxvirus, or adenovirus. U.S. Pat. No. 5,716,822 to Wardley et al. provides a method for inserting DNA encoding the feline calicivirus strain CFI/68 FIV capsid antigen into the feline herpesvirus thymidine kinase gene. Other recombinant virus vector vaccines embraced by the present invention, include but are not limited to, adenovirus, adeno-associated virus, parvovirus, and various poxvirus vectors to express the FCV-U1 or FCV-U2 capsid antigen or immunogenic fragment thereof. In particular, the present invention includes recombinant poxvirus vector vaccines that express the FCV-1 or FCV-2 capsid antigen or immunogenic fragment thereof made according to the methods taught in any one of U.S. Pat. Nos. 5,338,683 and 5,494,807 to Paoletti et al., which teach recombinant virus vaccines consisting of either vaccinia virus or canary poxvirus expressing foreign antigens; U.S. Pat. No. 5,266,313 to Esposito et al., which teaches recombinant raccoon poxvirus vectors expressing rabies virus antigens; and U.S. Pat. No. 6,010,703 to Maes et al., which teaches recombinant racoon poxvirus vectors that express the gD or gB feline herpesvirus antigens.

For any of the aforementioned recombinant virus vectors, the cDNA encoding the FCV-U1 or FCV-U2 capsid antigen or immunogenic fragment thereof is operably linked to a eukaryote promoter at the 5' end of the cDNA encoding the antigen and a eukaryote termination signal and poly(A) signal at the 3' end of the cDNA encoding the antigen. As used herein, the term "operably linked" means that the polynucleotide of the present invention (as a cDNA molecule) and a polynucleotide (DNA) containing an expression control sequence, e.g., transcription promoter and termination sequences, are situated in a vector or cell such that expression of the antigen encoded by the cDNA is regulated by the expression control sequence. Methods for cloning DNA such as the cDNA encoding the FCV-U1 or FCV-U2 capsid antigen or immunogenic fragment thereof and operably linking DNA containing expression control sequences thereto are well known in the art. Examples of promoters suitable for expressing the FCV-U1 or FCV-U2 capsid antigen or immunogenic fragment thereof in the recombinant virus vectors are the cytomegalovirus immediate-early (CMV) promoter, the Rous sarcoma virus long terminal repeat (RSV-LTR) promoter, the simian virus 40 (SV40) immediate-early promoter, and inducible promoters such as the metallothionein promoter. An example of a DNA having a termination and poly(A) signal is the SV40 late poly(A) region. Another example of a viral expression system suitable for producing the antigen is the Sindbis Expression system available from Invitrogen. The use of these commercially available expression vectors and systems are well known in the art.

In an embodiment further still of the present invention, the vaccine is provided as a nucleic acid or DNA molecule vaccine that elicits an active immune response in the cat. The DNA molecule vaccine consists of DNA having a nucleic acid sequence which encodes the capsid antigen or immunogenic fragment thereof of FCV-U1 or FCV-U2 or mutant thereof. In a preferred embodiment, the DNA molecule vaccine comprises the nucleic acid sequence selected from the group consisting of SEQ ID NO:1, SEQ ID NO:3, SEQ ID NO:5, and fragment thereof. The nucleic acid encoding the capsid antigen or immunogenic fragment thereof is operably linked at or near the start codon for the capsid antigen to a promoter that enables transcription of the capsid antigen or immunogenic fragment thereof from the nucleic acid when the nucleic acid is inoculated into the cells of the cat. Preferably, the DNA molecule is in a plasmid. Promoters that are useful for DNA vaccines are well known in the art and include, but are not limited to, the RSV LTR promoter, the CMV immediate early promoter, and the SV40 T antigen promoter. It is further preferred that the nucleic acid be operably linked at or near the termination codon of the sequence encoding the capsid antigen or immunogenic fragment thereof to a nucleic acid fragment comprising a transcription termination signal and poly(A) recognition signal. The DNA vaccine is provided to the cat in an accepted pharmaceutical carrier or in a lipid or liposome carrier similar to those disclosed in U.S. Pat. No. 5,703,055 to Felgner. The DNA vaccine can be provided to the cat by a variety of methods such as intramuscular injection, intrajet injection, or biolistic bombardment. Making DNA vaccines and methods for their use are provided in U.S. Pat. Nos. 5,589,466 and 5,580,859, both to Felgner. Finally, a method for producing pharmaceutical grade plasmid DNA is taught in U.S. Pat. No. 5,561,064 to Marquet et al.

Therefore, using the abovementioned methods, DNA vaccines that express the FCV-U1 or FCV-U2 capsid antigen or immunogenic fragment thereof are used to immunize cats against virulent feline calicivirus. The advantage of the DNA vaccine is that the DNA molecule is conveniently propagated as a plasmid which is a simple and inexpensive means for producing a vaccine, and since the vaccine is not live, many of the regulatory issues associated with live recombinant virus vector vaccines are not an issue with DNA vaccines. One skilled in the art would appreciate that the DNA vaccine of the present invention can comprise synthetically produced nucleic acids which are made by chemical synthesis methods well known in the art.

In an embodiment further still of the present invention, the vaccine consists of the isolated and purified capsid antigen or immunogenic fragment thereof of FCV-U1 or FCV-U2 or mutant thereof. In particular, a vaccine wherein the capsid antigen or immunogenic fragment thereof comprises the amino acid sequence selected from the group consisting of SEQ ID NO:2, SEQ ID NO:4, and SEQ ID NO:6. Preferably, the capsid antigen or immunogenic fragment thereof is produced in a recombinant bacterium or eukaryote expression vector which produces the antigen which is isolated and purified to make the vaccine. For example, the FCV-U1 or FCV-U2 capsid antigen or immunogenic fragment thereof is produced in a microorganism such as bacteria, yeast, or fungi; in a eukaryote cell such as a mammalian or an insect cell; or, in a recombinant virus vector such as adenovirus, poxvirus, herpesvirus, Simliki forest virus, baculovirus, bacteriophage, sindbis virus, or sendai virus. Suitable bacteria for producing the FCV-U1 or FCV-U2 capsid antigen or immunogenic fragment thereof include *Escherichia coli, Bacillus subtilis*, or any other bacterium that is capable of expressing heterologous polypeptides. Suitable yeast types for expressing the FCV-U1 or FCV-U2 capsid antigen or immunogenic fragment thereof include *Saccharomyces cerevisiae, Schizosaccharomyces pombe*, Candida, or any other yeast capable of expressing heterologous polypeptides. Methods for using the aforementioned bacteria, recombinant virus vectors, eukaryote cells to produce antigens for vaccines are well known in the art.

To produce the vaccine consisting of the capsid antigen or immunogenic fragment thereof, the nucleic acid encoding the FCV-U1 or FCV-U2 capsid antigen or immunogenic fragment thereof is in a plasmid and the nucleic acid is operably linked to a promoter which effects the expression of the capsid antigen or immunogenic fragment thereof in a microorganism. Suitable promoters include, but are not limited to, T7 phage promoter, T3 phage promoter, β-galactosidase promoter, and the Sp6 phage promoter. Expression of the FCV-U1 or FCV-U2 capsid antigen or immunogenic fragment thereof in a microorganism enables the capsid antigen to be produced using fermentation technologies which are used commercially for producing large quantities of recombinant antigenic polypeptides. Methods for isolating and purifying antigens are well known in the art and include methods such as gel filtration, affinity chromatography, ion exchange chromatography, or centrifugation.

To facilitate isolation of the FCV-U1 or FCV-U2 capsid antigen or immunogenic fragment thereof, a fusion polypeptide is made wherein the capsid antigen or immunogenic fragment thereof is linked to another polypeptide which enables isolation by affinity chromatography. Preferably, a fusion polypeptide is made using one of the expression systems infra. For example, the cDNA nucleic acid sequence encoding the FCV-U1 or FCV-U2 capsid antigen or immunogenic fragment thereof is linked at either the 5' end or 3' end to a nucleic acid encoding a polypeptide. The nucleic acids are linked in the proper codon reading frame to enable production of a fusion polypeptide wherein the amino and/or carboxyl terminus of the capsid antigen or portion thereof is fused to a polypeptide which allows for the simplified recovery of the antigen as a fusion polypeptide. The fusion polypeptide can also prevent the antigen from being degraded during purification. While a vaccine comprising the fusion polypeptide is efficacious, in some instances it can be desirable to remove the second polypeptide after purification. Therefore, it is also contemplated that the fusion polypeptide comprise a cleavage site at the junction between the antigen and the polypeptide. The cleavage site consists of an amino acid sequence that is cleaved with an enzyme specific for the amino acid sequence at the site. Examples of such cleavage sites that are contemplated include the enterokinase cleavage site which is cleaved by enterokinase, the factor Xa cleavage site which is cleaved by factor Xa, and the GENENASE cleavage site which is cleaved by GENENASE (GENENASE is a trademark of New England Biolabs, Beverly, Mass.). The following are methods for producing the capsid antigen or immunogenic fragment thereof as a fusion polypeptide or as an isolated antigen free of the polypeptide.

An example of a procaryote expression system for producing the FCV-U1 or FCV-U2 capsid antigen or immunogenic fragment thereof for use in vaccines is the Glutathione S-transferase (GST) Gene Fusion System available from Amersham Pharmacia Biotech, Piscataway, N.J., which uses the pGEX-4T-1 expression vector plasmid. The cDNA encoding the capsid antigen or immunogenic fragment thereof is fused in the proper codon reading frame with the DNA encoding GST. The GST part of the fusion polypeptide allows the rapid purification of the fusion polypeptide using glutathione Sepharose 4B affinity chromatography. After purification, the GST portion of the fusion polypeptide can be removed by cleavage with a site-specific protease such as thrombin or factor Xa to produce an antigen free of the GST polypeptide. The capsid antigen or immunogenic fragment thereof free of the GST polypeptide is produced by a second round of glutathione Sepharose 4B affinity chromatography.

Another method for producing a vaccine comprising the FCV-U1 or FCV-U2 capsid antigen or immunogenic fragment thereof is a method which links in-frame with the cDNA encoding the antigen, DNA codons that encode polyhistidine. The polyhistidine preferably comprises six histidine residues which allows purification of the fusion polypeptide by metal affinity chromatography, preferably nickel affinity chromatography. To produce the capsid antigen or immunogenic fragment thereof free of the polyhistidine, a cleavage site such as an enterokinase cleavage site is fused in the proper reading frame between the codons encoding the polyhistidine and the codons encoding the antigen. The antigen free of the polyhistidine is made by removing the polyhistidine by cleavage with enterokinase. The antigen free of the polyhistidine is produced by a second round of metal affinity chromatography which binds the free polyhistidine. This method was shown to be useful for preparing the LcrV antigen of Y. pestis which was disclosed in Motin et al. Infect. Immun. 64: 4313–4318 (1996). The Xpress System, available from Invitrogen, Carlsbad, California, is an example of a commercial kit which is available for making and then isolating polyhistidine-polypeptide fusion protein.

A method further still for producing a vaccine comprising the FCV-U1 or FCV-U2 capsid antigen or immunogenic fragment thereof uses a method disclosed by Motin et al., Infect. Immun. 64: 3021–3029 (1995). Motin et al. disclosed a DNA encoding a fusion polypeptide consisting of the DNA encoding an antigen linked to DNA encoding a portion of protein A wherein DNA encoding an enterokinase cleavage site is interposed in the proper codon reading frame between the DNA encoding protein A and the antigen. The protein A enables the fusion polypeptide to be isolated by IgG affinity chromatography, and the capsid antigen free of the protein A is produced by cleavage with enterokinase. The protein A is then removed by a second round of IgG affinity chromatography.

Another method for producing a vaccine comprising the FCV-U1 or FCV-U2 capsid antigen or immunogenic fragment thereof is based on methods disclosed in U.S. Pat. No. 5,725,863 to Daniels et al. The Daniels et al. method can be used to make the FCV-U1 or FCV-U2 vaccine which consists of enterotoxin molecule wherein each molecule has inserted therein upwards of 100 amino acid residues of the FCV-U1 or FCV-U2 capsid antigen. Other methods for making fusion polypeptide vaccines which can be used to make the vaccines of the present invention is disclosed in U.S. Pat. No. 5,585,100 to Mond et al. and U.S. Pat. No. 5,589,384 to Liscombe. Finally, the pMAL Fusion and Purification System available from New England Biolabs is another example of a method for making a fusion polypeptide wherein a maltose binding protein is fused to the capsid antigen or immunogenic fragment thereof. The maltose binding protein facilitates isolation of the fusion polypeptide by amylose affinity chromatography. The maltose binding protein can be linked to the antigen by one of the above mentioned cleavage sites which enables the antigen to be made free of the maltose binding protein.

While bacterial methods are used to produce the FCV-U1 or FCV-U2 capsid antigen or immunogenic fragment thereof for vaccines, it can be desirable to produce the capsid antigen or immunogenic fragment thereof in a eukaryote expression system. A particularly useful system is the baculovirus expression system which is disclosed in U.S. Pat. No. 5,229,293 to Matsuura et al. Baculovirus expression vectors suitable to produce the capsid antigen or immunogenic fragment thereof are the pPbac and pMbac vectors from Stratagene; and the Bac-N-Blue vector, the pBlueBac4.5 vector, pBlueBacHis2-A,B,C, and the pMelBac available from Invitrogen, Carlsbad, Calif.

Another eukaryote system useful for expressing the FCV-U1 or FCV-U2 capsid antigen or immunogenic fragment thereof for vaccines is a yeast expression system such as the ESP Yeast Protein Expression and Purification System available from Stratagene. Another yeast expression system is any one of the Pichia-based Expression systems from Invitrogen. Mammalian expression systems are also embraced by the present invention. Examples of mammalian expression systems are the LacSwitch II system, the pBK Phagemid, pXT1 vector system, and the pSG5 vector system from Stratagene; the pTargeT mammalian expression vector system, the pSI mammalian expression vector, pCI mammalian expression vector, and pAdVantage vectors available from Promega Corporation, Madison, Wis.; and the Ecdysone-Inducible Mammalian Expression System, pCDM8, pcDNA1.1, and pcDNA1.1/Amp available from Invitrogen.

The present invention further includes an embodiment consisting of vaccines that comprise the FCV-U1 or FCV-U2 capsid antigen or particular epitopes of the capsid antigen as components of a heat-stable spore delivery system made according to the method taught in U.S. Pat. No. 5,800,821 to Acheson et al. Therefore, the present invention provides a genetically engineered bacterial cell containing a nucleic acid encoding the FCV-U1 or FCV-U2 capsid antigen or immunogenic fragment thereof. When the recombinant bacterial spore vaccine is orally administered to the cat, the spores germinate in the gastrointestinal tract of the cat and the bacteria expresses the capsid antigen or immunogenic fragment thereof which comes into contact with the cat's immune system and elicits an immune response. The vaccine has the advantage of being heat stable; therefore, it can be stored at room temperature for an indefinite period of time.

While the above embodiments of the present invention provide active immunity against feline calicivirus, the present invention further comprises vaccines which provide passive immunity to feline calicivirus. A vaccine that elicits passive immunity against feline calicivirus consists of polyclonal antibodies or monoclonal antibodies that are against the FCV-U1 or FCV-U2 capsid antigen, immunogenic fragment thereof, or the whole FCV-U1 or FCV-U2 virus.

To make a passive immunity vaccine comprising polyclonal antibodies, the FCV-U1 or FCV-U2, capsid antigen thereof or immunogenic fragment thereof is injected into a suitable host for preparing the antibodies, preferably the host is a horse, swine, rabbit, sheep, or goat. Methods for producing polyclonal antibody vaccines from these hosts are well known in the art. By way of example, the capsid antigen or immunogenic fragment thereof or whole calicivirus FCV-U1 or FCV-U2 is admixed with an adjuvant such as Freund's complete or the less toxic TiterMax available from CytRx Corp., Norcross, Ga., which then administered to the host by methods well known in the art. Antibody production is monitored and when sufficient antibody has been produced, the serum is removed from the host and preferably, the antibody is recovered from the serum.

The passive immunity vaccine can comprise one or more monoclonal antibodies against one or more epitopes of the FCV-U1 or FCV-U2 capsid antigen or whole virus FCV-U1 or FCV-U2, or immunogenic fragment thereof. Methods and hybridomas for producing monoclonal antibodies are well known in the art. While monoclonal antibodies can be made using hybridoma technologies well known in the art, the monoclonal antibodies against the antigen can also be made according to phage display methods such as that disclosed in U.S. Pat. No. 5,977,322 to Marks et al. Felinized antibodies against the capsid antigen or portion thereof can be made according to methods which have been used for humanizing antibodies such as those disclosed in U.S. Pat. Nos. 5,693,762 and 5,693,761 both to Queen et al. A phage display kit that is useful for making monoclonal antibodies is the Recombinant Phage Antibody System available from Amersham Pharmacia Biotech.

An important aspect of any vaccination program is to be able to distinguish animals vaccinated against a disease from animals infected with the disease. Therefore, the present invention further includes methods or assays that distinguish cats vaccinated with the vaccine of the present invention from cats infected with a field strain of feline calicivirus, cats vaccinated with another commercial vaccine preparation, or cats never exposed to feline calicivirus. In general, the assays are either the immunologically-based antibody-capture or an antigen-capture assays.

In an antibody-capture assay to identify cats vaccinated with a vaccine of the present invention, a biological sample from the cat is tested for the presence of antibodies against feline calicivirus other than FCV-U1 or FCV-U2. The presence of antibodies in a biological sample against a feline calicivirus other than the FCV-U1 or FCV-U2 indicates the cat is infected with a feline calicivirus other than FCV-U1 or FCV-U2. Conversely, the presence of antibodies against FCV-U1 or FCV-U2 indicates the cat was vaccinated with the vaccine of the present invention. The assay can further include controls which comprise capsid antigens from other calicivirus strains such as the F-9 strain.

In an antigen-capture assay, a biological sample from a cat is assayed for the presence of capsid antigens which bind to monoclonal or polyclonal antibodies made against the FCV-U1 or FCV-U2 capsid antigen or immunogenic fragment thereof. In this assay, a cat vaccinated with the vaccine of the present invention produces antigens that react with the polyclonal or monoclonal antibodies against FCV-U1 or FCV-U2 whereas a non-vaccinated cat does not. The assay can further include controls which comprise antibodies against other feline calicivirus strains such as F-9. Thus, in an assay, a sample from a cat that had been vaccinated with the vaccine of the present invention will contain FCV-U1 or FCV-U2 antigens whereas a sample from a cat that is infected with, or exposed to, another feline calicivirus will not contain antibodies against the capsid antigen of the FCV-U1 or FCV-U2.

In general, the antibody-detection or antigen detection assays are performed using an enzyme-linked immunosorbent assay (ELISA) embodiment. For an antibody-capture ELISA, a microtiter plate is provided containing a plurality of wells wherein a first well or series of wells contains the capsid antigen of the FCV-U1 or FCV-U2 immobilized to the surface therein and a second well or series of wells contains antigens from another feline calicivirus strain (or capsid antigen from a commercially available calicivirus vaccine) immobilized to the surface therein. Next, the biological sample is added to the wells containing the bound antigens and antibodies against feline calicivirus are allowed to bind to form an antigen-antibody complex. The biological sample can be provided neat or in a limiting dilution series in a physiological solution. Unbound material in the sample is removed from the antibody-antigen complex by washing. The complex is then reacted with a labeled anti-species antibody or labeled monoclonal antibody that binds to feline antibodies to form an antigen-antibody-anti-species-antibody complex. This complex can be detected when the labeled monoclonal or polyclonal antibody is conjugated to a reporter ligand such as horseradish-peroxidase or alkaline phosphatase. Alternatively, the second monoclonal or polyclonal antibody can be conjugated to reporter ligands such as a fluorescing ligand, biotin, colored latex, colloidal gold magnetic beads, radioisotopes or the like. Detection is by methods well known in the art for detecting the particular reporter ligand. Therefore, a sample from a cat that had been vaccinated with the vaccine of the present invention will produce antibodies against only the FCV-U1 or FCV-U2 capsid antigen whereas a sample from a cat that is infected with, or exposed to, feline calicivirus will not contain antibodies against the capsid antigen of the FCV-U1 or FCV-U2.

For an antigen-capture ELISA, a microtiter plate is provided containing a plurality of wells wherein a first well or series of wells contains polyclonal or monoclonal antibodies against the capsid antigen or immunogenic fragment thereof of the FCV-U1 or FCV-U2 immobilized to the surface therein and a second well or series of wells contains antibodies against antigens of another feline calicivirus strain (or capsid antigen or immunogenic fragment thereof from a commercially available calicivirus vaccine) immobilized to the surface therein. Next, the biological sample is added to the wells containing the bound antibodies and antigens against feline calicivirus are allowed to bind to form an antibody-antigen complex. The biological sample can be provided neat or in a limiting dilution series in a physiological solution. Unbound material in the sample is removed from the antibody-antigen complex by washing. The complex is then reacted with a labeled polyclonal antibody or labeled monoclonal antibody against FCV-U1 or FCV-U2 or immunogenic fragment thereof which binds to feline antibodies to form a antibody-antigen-antibody complex. This complex can be detected when the labeled monoclonal or polyclonal antibody is conjugated to a reporter ligand such as horseradish-peroxidase or alkaline phosphatase. Alternatively, the labeled monoclonal or polyclonal antibody can be conjugated to reporter ligands such as a fluorescing ligand, biotin, colored latex, colloidal gold magnetic beads, radioisotopes or the like. Detection is by methods well known in the art for detecting the particular reporter ligand.

ELISA and its variations are well known in the art. The ELISA can be provided as a kit for distinguishing cats vaccinated with the vaccine of the present invention from unvaccinated cats, and from cats infected with feline calicivirus or vaccinated with a commercially available feline calicivirus vaccine.

Since it is important to be able to test samples in the field in order to distinguish cats infected with feline calicivirus from cats vaccinated with the vaccine of the present invention, the present invention further includes rapid immunodiffusion-based methods, their devices, and kits comprising the same. Therefore, the present invention can be provided with a kit that comprises any one of the methods described in U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486,530 to David et al., and U.S. Pat. No. 4,786,589 to Rounds et al. While the aforementioned disclose particular rapid immunodiffusion methods, the present invention is not to be construed to be limited to the aforementioned. It is within the scope of the present invention to embrace derivations and modifications of the aforementioned.

In another method for distinguishing cats vaccinated with the vaccine of the present invention from cats infected with, or exposed to feline calicivirus is to provide as the vaccine the aforementioned fusion polypeptide wherein the polypeptide comprises a marker epitope that elicits an antibody in the vaccinated cat that would not normally be present in the feline. For example, the marker epitope could be from a pathogen that does not infect cats or a synthetic polypeptide that elicits an antibody in cats that would not normally occur in cats. Therefore, if a sample from a cat contained antibodies against the marker epitope and the capsid antigen, the cat was vaccinated with the vaccine of the present invention. The sample is tested according to any of the aforementioned diagnostic methods.

In another method, determining whether a cat has been vaccinated with the vaccine of the present invention is by reverse transcriptase-polymerase chain reaction (RT-PCR). In general, feline calicivirus RNA is extracted from a biological sample using methods well known in the art. such as the Qiagen HCV Kit. The RT-PCR reaction is performed by any one of the methods well known in the art such as the BRL One-Step RT-PCR Kit (Life Technologies, Bethesda, Md.). The preferred RT-PCR primer pair flanks a target sequence from within the region of the viral genome encoding the capsid antigen. For example, a suitable RT-PCR primer pair is the upstream primer 5'-ATGGAATTTGGAACTGTTTGG-3' (SEQ ID NO:8) and the downstream primer 5'-GCTGAGCTTTACCAATAGTG-3' (SEQ ID NO:9). The PCR amplified products are resolved on Agarose gels containing ethidium bromide and visualized under UV light.

A method that is particularly useful in practicing the present invention is the PCR-based TAQMAN technology (Heid et al., *Genome Res.* 6: 986–994 (1996)). TAQMAN is a registered trademark of Roche Molecular Systems, Inc. (Alameda, Calif.). Methods and apparatus for performing TAQMAN-based reactions and detecting the reaction products are available from Applied Biosystems Division, Perkin-Elmer, Foster City, Calif. To use the TAQMAN method, the RT-PCR reaction is performed using TAQMAN technology in which case an oligonucleotide probe labeled at the 5' end with an energy donor fluor and at the 3' end with an energy quencher. The probe is complementary to a sequence within the target sequence which is about 100 nucleotides or less from either the upstream primer or the downstream primer. During the RT-PCR reaction, if a sample contains FCV-U1 or FCV-U2, the probe is degraded by the 5' exonuclease activity of the DNA polymerase which releases the energy donor fluor from the quenching effect of the quencher and the fluorescence of the energy donor fluor is detected. The use of dual-labeled oligonucleotide probes in PCR reactions is disclosed in U.S. Pat. No. 5,716,784 to DiCesare, which is hereby incorporated herein by reference.

The following examples are intended to promote a further understanding of the present invention.

EXAMPLE 1

This example shows a method which enables the isolation of viable feline calicivirus from urine from cats with idiopathic lower urinary tract disease (LUTD).

About 1 to 2 ml urine samples were collected by cystocentesis or by catherization. For urine samples less than 2 ml, the samples were brought up to 2 ml with serum-free Eagle's Minimal Essential medium (EMEM). The samples were refrigerated at 4° C. immediately after collection. Samples which contained large amounts of sediment were divided into two portions.

For all samples, the urine was concentrated. To concentrate the urine, 2 ml aliquots of the urine were added to the top chamber of sterile microconcentrators which were centrifuged at 6,500 rpm for 30 minutes at 4° C. The samples were centrifuged using an SS-34 fixed-angle Sorvall rotor in a Sorvall RC-5B refrigerated centrifuge without the brake. The flow-through volume was discarded and the concentrator retentate was resuspended to a final volume of 1.1 ml each with EMEM containing 20% fetal calf serum (EMEM-20% FCS). The suspension was pipetted repeated to wash the filter in the concentrator. The suspension was transferred to a sterile 1.5 ml cryovial or Eppendorf microcentrifuge tube and refrigerated at 4° C. The samples were inoculated onto CRFK cells for virus isolation within 48 hours of preparation.

The CRFK cells for virus isolation were prepared from F-75 flasks as follows. The media from a flask containing CRFK cell monolayers was removed and the cells washed once with alkaline chelating solution (ACS). The ACS was removed and 4 ml of ACS containing about 0.025% of trypsin was added. The cells were thoroughly coated with the ACS containing trypsin and the excess was removed. The cells were incubated for 2 to 3 minutes at 37° C. to loosen the cells. The monolayer was detached by firmly tapping the flask and 7 ml of EMEM containing 10% FCS (EMEM-10% FCS) was added. The cells were homogenized in the media by repeated pipetting. The cells were transferred to a 15 ml tube and allowed to settle for 5 minutes. 0.8 to 1 ml of a 1:7 split was adequate to make 10 heavily seeded roller tubes of cells. Thus, 0.8 ml of the cell suspension was added to 12 ml of EMEM-10% FCS to make 10 roller tubes. 6 ml was drawn up and 1.2 ml was added to each of 5 roller tubes. The tubes were capped tightly, the walls of the roller tube coated with the cell suspension and incubated at 37° C. for 48 hours. A new F-75 flask was made by added 1 ml of the cell suspension to 17 ml EMEM-10% FCS and transferred to an F-75 flask.

The above urine samples were sonicated in a sonicator to release the virus. A sonicator probe was sterilized with ethanol, dried, and immersed into the sample. The power was slowly increased to 30%. The sample was sonicated for 10 seconds which was repeated. Afterwards, the urine was filtered through a 0.45 μm filter into a new tube. Foam formation was avoided.

To inoculate the roller tubes prepared above, first, 0.5 ml of serum-free EMEM was added to each roller tube. Then 0.3 ml of urine was added to 3 roller tubes or 0.45 ml of concentrated urine was added to 2 roller tubes. One roller tube was kept as an uninoculated control. The samples were allowed to adsorb for 1 hour at room temperature. Afterwards, the media was removed and the cells washed once with serum-free EMEM before adding 2.5 ml of EMEM-10% FBS. The roller tubes were incubated at 37° C.

To detect feline calicivirus, the roller tubes were examined daily for cytopathic effect (CPE) for 7 days. Before a sample was considered negative for feline calicivirus, the inoculated cells were passed at least 3 times. For each passage of the inoculated cells, the cells were freeze-thawed 3 times and the freeze-thaw sample was allowed to settle for 5 minutes. Then media was removed from a fresh roller bottle prepared as above and 0.3 ml of the freeze-thaw sample and 0.2 ml of serum-free media was added to the bottle. Two tubes were prepared for each freeze-thaw sample. The freeze-thaw samples were allowed to adsorb for 1 hour at room temperature. Afterwards, the media was removed and 2.2 ml of EMEM-10% FBS was added. The roller tubes were incubated at 37° C. and the cells were examined daily for CPE for 7 days. Feline calicivirus isolates were identified by electron microscopy and RT-PCR. Virus stocks were prepared from cell samples that were positive for feline calicivirus.

Virus stocks were prepared as follows. Cultures comprising monolayers of CRFK cells were prepared in T-75 flasks in EMEM to about 98% confluence and inoculated with $10^{-4}$ to $10^{-5}$ dilutions of virus. On the third day post-inoculation when cytopathic effect (CPE) was about 95% or more, the cultures were harvested. The cells were centrifuged at 2,000 rpm for 10 minutes at 4° C. Afterwards, the supernatant fraction containing virus was removed to a new tube. The cell pellet was resuspended in about 1 ml of the supernatant fraction and the suspension freeze-thawed three times. The cell debris was pelleted as above and the supernatant fraction was pooled with the first supernatant fraction. Fetal bovine serum and dimethylsulfoxide (DMSO) was added to the pooled supernatant fraction to provide a suspension containing a final serum concentration of 20% and a final DMSO concentration of 10%. The suspension was divided into aliquots and stored frozen at −80° C. or lower.

Table 1 shows the effect of urine sample handling on detection of feline calicivirus. The table compares samples prepared without concentration to samples concentrated 10-fold. The RNA for RT-PCR was extracted with a Qiagen HCV Kit. RT-PCR was performed as described in Example 2.

TABLE 1

| Sample | Low Speed Spin | 10x Concentrator | RT-PCR |
| --- | --- | --- | --- |
| Urine + FCV | no | no | +− |
|  |  | yes | − |
|  | yes | no | + |
|  |  | yes | − |
| Medium + FCV | no | no | + |
|  |  | yes | + |

FCV is feline calicivirus.

Table 1 shows that urine samples concentrated 10-fold in a concentrator rendered the feline calicivirus undetectable by RT-PCR whereas detecting feline calicivirus in medium was unaffected by a 10-fold concentration. This is suspected to be caused by the co-concentration of urine components that inhibit RT-PCR. Removal of sediment by a low speed spin in a centrifuge had no significant effect of detection.

EXAMPLE 2

This example shows the procedure for RT-PCR detection of feline calicivirus. RNA was isolated using the RNEASY Kit Total RNA Isolation Kit from Qiagen, Inc.

The RT-PCR protocol was performed as follows. The reverse transcription was performed in a 20 μl volume containing 4 μl of X buffer; 1 μl of a 10 mM deoxynucleotide solution containing 10 mM of each deoxynucleotide triphosphate (adenosine triphosphate, guanosine triphosphate, cytosine triphosphate, and thymidine triphosphate); 0.5 μl RNasin (from Promega Corp., Madison, Wis.); 1 μl each of primers SEQ ID NO:8 and SEQ ID NO:9; 0.5 μl AMV reverse transcriptase (GIBCO-BRL); RNA which had been linearized at 65° C. for 5 minutes, and distilled water to bring the reaction to 20 μl. The reaction was incubated at 50° C. for 1.5 hours. Afterwards, 3 μl of the reverse transcription reaction was added to a solution containing 30 μl of 3.3× buffer; 6 μl of 25 mM Mg(OAc)$_2$; 1 μl of the above deoxynucleotide solution; 1 μl each of the above primers, 1 μl of high fidelity rTth DNA polymerase XL (Perkin Elmer Applied Biosystems); and 57 μl distilled water. The PCR reaction was 94° C. for 5 minutes followed by 40 cycles wherein each cycle consisted of the steps; 94° C. for 1 minute, 50° C. for 1 minute, and 72° C. for 1 minute. Afterwards, a tailing reaction was performed using 0.8 μl Taq DNA polymerase (GIBCO-BRL) and incubating at 72° C. for 10 minutes. The RT-PCR results were visualized on agarose gels stained with ethidium bromide.

Table 2 shows the specificity of the R-PCR method for detecting feline calicivirus in samples known to contain feline calicivirus. Samples 17 and 24 are FCV-U1 and FCV-U2, respectively. The table shows that the RT-PCR method has a specificity of 87% (21 positive samples out of 24 samples assayed). Samples 25–27 were cross-contaminated and were not included in the sensitivity calculations.

amplified in a 50 μl RT-PCR reaction. 10 μl of each RT-PCR product was analyzed by agarose gel electrophoresis. The results show that the method is sensitive with the best results for RNA that was extracted from samples at 4° C. for one hour and RNA that was extracted with the Qiagen RNEASY Kit.

TABLE 3

| Sample | Temp/Time | Dilution | | | | | | | |
|---|---|---|---|---|---|---|---|---|---|
| | | −1 | −2 | −3 | −4 | −5 | −6 | −7 | −8 |
| FCV #10 + water | 4° C./1 hr | + | + | + | − | − | − | − | − |
| FCV #5 + urine* | 4° C./1 hr | + | + | +/− | − | − | − | − | − |
| FCV #5 + urine* | 37° C./1 hr | + | + | + | ND | ND | ND | ND | ND |
| FCV #5 + urine* | 37° C./6 hr | + | + | + | ND | ND | ND | ND | ND |
| FCV #5 + urine* | 37° C./12 hr | + | + | + | ND | ND | ND | ND | ND |
| FCV #5 + urine* | 37° C./24 hr | + | + | − | ND | ND | ND | ND | ND |
| FCV #5 + urine¶ | 4° C./1 hr | + | + | + | + | + | + | ND | ND |

*RNA extraction with Qiagen HCV Kit after low speed centrifugation and freezing at −70° C.
¶RNA extraction with Qiagen RNEASY Kit after freezing at −70° C. without low speed centrifugation.

TABLE 2

| Isolate | ADHL # | Titer (TCID$_{50/ml}$ × 10$^{-7}$) | RT-PCR |
|---|---|---|---|
| 1 | 1459461 | 1.52 | + |
| 2 | 1467733 | 2.5 | + |
| 3 | 1494363 | 7.2 | + |
| 4 | 1502752 | 22.4 | + |
| 5 | 1516507 | 40 | + |
| 6 | 1524133 | 180 | + |
| 7 | 1529083-1 | 224 | + |
| 8 | 1533786 | 72 | + |
| 9 | 1586997 | 12.8 | + |
| 10 | 1658844 | 33.2 | negative |
| 11 | 1759144 | ND | + |
| 12 | 1762174 | ND | + |
| 13 | 1808813 | ND | + |
| 14 | 1809896-2 | ND | + |
| 15 | 1821129 | ND | negative |
| 16 | 2005062 | ND | + |
| 17 | 1903867 | 13.6 | + |
| 18 | 1976866 | ND | + |
| 19 | 1978045 | ND | negative |
| 20 | 2041261 | ND | + |
| 21 | 2043642 | ND | + |
| 22 | 2057993 | ND | + |
| 23 | 2069758 | ND | + |
| 24 | 2089726 | ND | + |
| 25 | 2095787 | ND | + (cross-contaminant) |
| 26 | 2096335-1 | ND | + (cross-contaminant) |
| 27 | 2096335-2 | ND | + (cross-contaminant) |

Table 3 shows the sensitivity of the RT-PCR method for detecting feline calicivirus in urine samples. The stock virus was FCV#5 which had a titer of 4×10$^8$ TCID$_{50/ml}$. Serial dilutions were made in urine or medium. RNA was extracted from 140 μl aliquots of each suspension with a Qiagen HCV Kit or the RNEASY Kit. 5 μl of the extracted RNA was

EXAMPLE 3

This example provides a method for producing an attenuated FCV-U1 or FCV-U2.

The FCV-U1 or FCV-U2 is serially passed in CRFK cells as shown in Example 1. Briefly, to each tissue culture flask containing a monolayer of CRFK cells is added an inoculum of FCV-U1 or FCV-U2 prepared as in Example 1. The seeded flasks are maintained at 37° C. until CPE is observed by microscopic examination (between 2 and 7 days). When CPE reaches between about 75–90 percent of the monolayer, the contents of the tube are harvested and 0.2 ml inoculums are subjected to identical serial passages. At appropriate passage intervals, virus is isolated and tested in cats for typical signs of feline calicivirus infection and for an immune response to the virus. To determine whether the virus still causes disease in cats, 1 ml of a vaccine prepared according to Example 4 and titrated to a virus titer at 37° C. of 10$^3$ to 10$^8$ TCID$_{50/ml}$ (determined by CPE) is administered oronasally to three susceptible cats. Two other cats are maintained as controls. All 5 cats are previously determined to be sero-negative for feline calicivirus. When virus from a particular passage level is determined to not cause disease in cats, the virus at that passage level is attenuated. An attenuated virus which stimulates an immune response is appropriate for use as a vaccine.

While EMEM is the medium used herein, it is understood that other culture mediums can used. Further, while CRFK cells are used herein other cells can be used, such as feline diploid tongue cell line Fc3Tg or Crandell's Feline Kidney (CrFK) cells. In addition to flasks, the virus can be attenuated using roller tubes.

EXAMPLE 4

This example provides a method for producing a vaccine of FCV-U1 or FCV-U2. Growing conditions of the cells and virus are as in Example 1.

To each roller tube containing a monolayer of CRFK cells is added an inoculum of FCV-U1 or FCV-U2 prepared as in Example 1. The seeded roller tubes are maintained at 37° C. until CPE is observed by microscopic examination (between 2 and 7 days). When CPE reaches between about 75–90 percent of the monolayer, the contents of the tube are harvested and 0.2 ml inoculums are subjected to identical serial passages for about 6 additional passages. After the last passage, a standard terminal dilution purification is performed using EMEM supplemented with antibiotics (30 units penicillin, 30 μg streptomycin and 2.5 μg amphotericin) as the diluent with incubation maintained at 37° C. After 7 days, the final flask which shows 75 to 90% CPE is harvested and the entire procedure repeated twice for a total of 10 passages. An 11th passage is performed for purposes of increasing volume by inoculating a 0.5 ml sample from the 10th passage into flasks containing CRFK monolayers. At the end of the 11th passage, the pool is harvested, identified, and titrated by methods known in the art.

The pool thus prepared is the bulk vaccine which can be diluted according to titer or can have added to it stabilizers or other nontoxic substances. For use as a vaccine, it can be desiccated or prepared in liquid form.

In propagating the virus, any tissue culture medium that is nontoxic to cats can be used. While the virus was prepared in roller tubes, it is understood that other methods and containers for propagating viruses on cell monolayers can be used.

It is also appreciated that in preparing vaccine it would be impractical to start with virus isolated from an infected cat. Therefore, this invention embodies the method of preparing feline calicivirus vaccine using as the starting virus one that has already undergone modification by serial passages in feline tissue cultures as described above. Thus, the vaccine that is prepared contains virus that may be modified, mutated, or attenuated, depending on passage level, when compared to the virus isolated from the cat. As a practical matter, to the extent that the virus has been mutated by passage in cell culture, the vaccine of the present invention may comprise a mutant feline calicivirus. Thus, it is appropriate to refer to the vaccine of the present invention as comprising FCV-U1 or FCV-U2 or mutant thereof.

EXAMPLE 5

This example illustrates a test for evaluating the efficacy of the FCV-U1 or FCV-U2 vaccine.

1 ml of a vaccine prepared according to Example 4 and titrated to a virus titer at 37° C. of $10^3$ to $10^8$ TCID$_{50/ml}$ (determined by CPE) is administered intramuscularly to three susceptible cats. Two other cats are maintained as controls. All 5 cats are previously determined to be seronegative for feline calicivirus. One month post-vaccination, a serum sample is removed from the cats and tested for antibodies against feline calicivirus. An antibody titer against feline calicivirus that is greater than the unvaccinated control cats indicates that the vaccination successfully induces an immune response.

The cats are then challenged oronasally with virulent feline calicivirus (F-9) applied by a nebulizer. Each cat is in an enclosed atmosphere and is given a total dose of about $10^6$ TCID$_{50}$. The cats are observed for clinical signs of clinical disease and observed for a longer period of time for manifestations of LUTD.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A vaccine for immunizing cats against feline calicivirus comprising:

FCV-U1 or mutant thereof, in an effective amount to produce an immune response, and a pharmaceutically acceptable carrier.

2. The vaccine of claim 1 containing an adjuvant.

3. The vaccine of claim 1 or 2, wherein the FCV-U1 or mutant thereof is live.

4. The vaccine of claim 1 or 2, wherein the FCV-U1 or mutant thereof is attenuated.

5. The vaccine of claim 1 or 2, wherein the FCV-U1 or mutant thereof is inactivated.

6. The vaccine of claim 1 or 2, comprising the FCV-U2 or mutant thereof and at least one feline calicivirus strain selected from the group consisting of FCV-U2, FCV-F9, FCV-LLK, FCV-M8, FCV-255, and FCV-2280, in addition to the FCV-U1 or mutant thereof.

7. A vaccine for immunizing cats against feline calicivirus comprising:

FCV-U2 or mutant thereof, in an effective amount to produce an immune response, and a pharmaceutically acceptable carrier.

8. The vaccine of claim 7 containing an adjuvant.

9. The vaccine of claim 7 or 8, wherein the FCV-U2 or mutant thereof is live.

10. The vaccine of claim 7 or 8, wherein the FCV-U2 or mutant thereof is attenuated.

11. The vaccine of claim 7 or 8, wherein the FCV-U2 or mutant thereof is inactivated.

12. The vaccine of claim 7 or 8, comprising the FCV-U2 or mutant thereof and at least one feline calicivirus strain selected from the group consisting of FCV-U1, FCV-F9, FCV-LLK, FCV-M8, FCV-255, and FCV-2280, in addition to the FCV-U2or mutant thereof.

13. A method for immunizing a cat against feline calicivirus comprising:

administering to the cat an effective dose of a vaccine selected from the group consisting of a live FCV-U1 or mutant thereof and a killed FCV-U1 or mutant thereof, in a pharmaceutically acceptable carrier.

14. The method of claim 13, wherein the capsid antigen or immunogenic fragment thereof comprises the amino acid sequence selected from the group consisting of SEQ ID NO:2, SEQ ID NO:4, and SEQ ID NO:6.

15. The method of claim 13, wherein the nucleotide sequence comprises the nucleotide sequence selected from the group consisting of SEQ ID NO:1, SEQ ID NO:3, and SEQ ID NO:5.

16. A method for immunizing a cat against feline calicivirus comprising:

administering to the cat an effective dose of a vaccine selected from the group consisting of a live FCV-U2 or mutant thereof and a killed FCV-U2 or mutant thereof, in a pharmaceutically acceptable carrier.

17. An isolated and purified culture of feline calicivirus FCV-UV1 or mutant thereof deposited as ATCC PTA-3444.

18. An isolated and purified culture of feline calicivirus FCV-UV2 or mutant thereof deposited as ATCC PTA-3445.

* * * * *

SEQUENCE LISTING

```
<160> NUMBER OF SEQ ID NOS: 9

<210> SEQ ID NO 1
<211> LENGTH: 1926
<212> TYPE: DNA
<213> ORGANISM: Feline calicivirus

<400> SEQUENCE: 1
atggaatttg gaactgtttg ggactgtaac cagtcaccat tggaaattta tctagagtcc      60
atccttggag atgatgaatg ggcctccact tatgatgcaa ttgacccgc agttccacca     120 atgcactggg atgatgctgg aaagattttc cagccacacc ctggtgtgct gatgcaccac     180
ctcattgcaa aggttgctga ggcttgggat ccagatctac ctctctttcg tttggagggt     240
gatgatggat caatcacaac acctgagcag ggaacaatgg ttggtgggt aattgctgaa     300 cccagcgctc aaatgtcggc agctgccgac atggccacag ggaagagcgt tgactctgag     360
tgggaagctt tcttctcctt tcacaccagc gtcaactgga gcacatctga aactcaagga     420
aagattctct ttaaacaatc tttaggaccc ttactcaatc cctatctttc tcatctgca     480 aaactctatg tcgcttggtc tggttctgtt gaggtaagat tttctatttc cggatctggc     540
gtgttcgggg ggaaattggc tgctattgtt gtgccaccag gcattgaacc tgttcaaagc     600
acatcaatgc ttcaataccc gcatgttctc ttcgacgctc gccaggttga gcctgtcatc     660
tttgctattc ctgatttaag gagcaatcta tatcacctaa tgtccgacac tgacactaca     720
```

-continued

```
tcccttgtaa ttatggtgta taatgatctt atcaaccctt atgctaatga cacaaactct     780
tctggctgta tcgtcactgt tgagacaaaa cctggtcctg atttcaagtt tcacctctta     840
aaaccacctg gatctatgct aacacatggg tcagtacctt ctgatctaat ccctaaatca     900
tcttctctct ggattggtaa tcgccattgg tctgacatta ctgatttcat catacgtcct     960
tttgtctttc aagcgaatcg acactttgac tttaaccagg aaactgctgg gtggagtacg    1020
ccgagattcc gaccaataac catcacagtt agtgagagca acatgtcaaa actcggaata    1080
ggtgttgcaa ctgactacat tgtccctggg atcccggacg gctggcctga cacaacaatc    1140
ccagagcagc tcacccctgc aggtatatac tcaatcacag caagtaatgg cactgtcatc    1200
accacggccg caggctatga tgctgcagaa acaatcgtaa acacaacaaa cttcaaaagc    1260
atgtacattt gtgggtcatt gcaaagagcc tggggtgata agaaaatctc aaacactgct    1320
tttataacca cagcagtcag aaaaggtaac tcgatcgagc catcaaacac aattgacatg    1380
acaaagcttg tcgtgtacca ggatgcacat gtgggtgaag aagtccaaac ctccgacatc    1440
actcttgcac ttcttggtta cacgggaatt ggtgaagaag caattggttc agacagagat    1500
aaagtggtgc ggatcagtgt ccttccagaa actggtgccc gtggtggtaa tcaccctatc    1560
ttttataaaa attcgattaa attgggttat gtgattaggt caattgatgt gtttaactct    1620
cagattctgc acacctcaag gcagctatcc ttaaacaact atctactccc tccagattct    1680
tttgcagtct atagaatact tgactctaat ggttcatggt ttgatattgg tattgatact    1740
gatggctttt cttttgttgg tgtatctaac ttacctaaac tagagtttcc tctttctgcc    1800
ccctacatgg gaattcagct ggctaaggtt cgccttgcct ctaacattag gagtagtatg    1860
actaaattat gaattcaata ttgggcttaa ttgatactgt tacaaacact attggtaaag    1920
ctcagc                                                               1926
```

```

<210> SEQ ID NO 2
<211> LENGTH: 623
<212> TYPE: PRT
<213> ORGANISM: Feline calicivirus

<400> SEQUENCE: 2

Met Glu Phe Gly Thr Val Trp Asp Cys Asn Gln Ser Pro Leu Glu Ile
  1               5                  10                  15

Tyr Leu Glu Ser Ile Leu Gly Asp Asp Glu Trp Ala Ser Thr Tyr Asp
             20                  25                  30

Ala Ile Asp Pro Ala Val Pro Pro Met His Trp Asp Asp Ala Gly Lys
         35                  40                  45

Ile Phe Gln Pro His Pro Gly Val Leu Met His His Leu Ile Ala Lys
     50                  55                  60

Val Ala Glu Ala Trp Asp Pro Asp Leu Pro Leu Phe Arg Leu Glu Gly
 65                  70                  75                  80

Asp Asp Gly Ser Ile Thr Thr Pro Glu Gln Gly Thr Met Val Gly Gly
                 85                  90                  95

Val Ile Ala Glu Pro Ser Ala Gln Met Ser Ala Ala Ala Asp Met Ala
            100                 105                 110

Thr Gly Lys Ser Val Asp Ser Glu Trp Glu Ala Phe Phe Ser Phe His
        115                 120                 125

Thr Ser Val Asn Trp Ser Thr Ser Glu Thr Gln Gly Lys Ile Leu Phe
    130                 135                 140

Lys Gln Ser Leu Gly Pro Leu Leu Asn Pro Tyr Leu Ser His Leu Ala
145                 150                 155                 160
```

-continued

```
Lys Leu Tyr Val Ala Trp Ser Gly Ser Val Glu Val Arg Phe Ser Ile
            165                 170                 175
Ser Gly Ser Gly Val Phe Gly Gly Lys Leu Ala Ala Ile Val Val Pro
            180                 185                 190
Pro Gly Ile Glu Pro Val Gln Ser Thr Ser Met Leu Gln Tyr Pro His
            195                 200                 205
Val Leu Phe Asp Ala Arg Gln Val Glu Pro Val Ile Phe Ala Ile Pro
            210                 215                 220
Asp Leu Arg Ser Asn Leu Tyr His Leu Met Ser Asp Thr Asp Thr Thr
225                 230                 235                 240
Ser Leu Val Ile Met Val Tyr Asn Asp Leu Ile Asn Pro Tyr Ala Asn
            245                 250                 255
Asp Thr Asn Ser Ser Gly Cys Ile Val Thr Val Glu Thr Lys Pro Gly
            260                 265                 270
Pro Asp Phe Lys Phe His Leu Leu Lys Pro Pro Gly Ser Met Leu Thr
            275                 280                 285
His Gly Ser Val Pro Ser Asp Leu Ile Pro Lys Ser Ser Ser Leu Trp
            290                 295                 300
Ile Gly Asn Arg His Trp Ser Asp Ile Thr Asp Phe Ile Ile Arg Pro
305                 310                 315                 320
Phe Val Phe Gln Ala Asn Arg His Phe Asp Phe Asn Gln Glu Thr Ala
            325                 330                 335
Gly Trp Ser Thr Pro Arg Phe Arg Pro Ile Thr Ile Thr Val Ser Glu
            340                 345                 350
Ser Asn Met Ser Lys Leu Gly Ile Gly Val Ala Thr Asp Tyr Ile Val
            355                 360                 365
Pro Gly Ile Pro Asp Gly Trp Pro Asp Thr Thr Ile Pro Glu Gln Leu
            370                 375                 380
Thr Pro Ala Gly Ile Tyr Ser Ile Thr Ala Ser Asn Gly Thr Val Ile
385                 390                 395                 400
Thr Thr Ala Ala Gly Tyr Asp Ala Ala Glu Thr Ile Val Asn Thr Thr
            405                 410                 415
Asn Phe Lys Ser Met Tyr Ile Cys Gly Ser Leu Gln Arg Ala Trp Gly
            420                 425                 430
Asp Lys Lys Ile Ser Asn Thr Ala Phe Ile Thr Thr Ala Val Arg Lys
            435                 440                 445
Gly Asn Ser Ile Glu Pro Ser Asn Thr Ile Asp Met Thr Lys Leu Val
            450                 455                 460
Val Tyr Gln Asp Ala His Val Gly Glu Glu Val Gln Thr Ser Asp Ile
465                 470                 475                 480
Thr Leu Ala Leu Leu Gly Tyr Thr Gly Ile Gly Glu Glu Ala Ile Gly
            485                 490                 495
Ser Asp Arg Asp Lys Val Val Arg Ile Ser Val Leu Pro Glu Thr Gly
            500                 505                 510
Ala Arg Gly Gly Asn His Pro Ile Phe Tyr Lys Asn Ser Ile Lys Leu
            515                 520                 525
Gly Tyr Val Ile Arg Ser Ile Asp Val Phe Asn Ser Gln Ile Leu His
            530                 535                 540
Thr Ser Arg Gln Leu Ser Leu Asn Asn Tyr Leu Leu Pro Pro Asp Ser
545                 550                 555                 560
Phe Ala Val Tyr Arg Ile Leu Asp Ser Asn Gly Ser Trp Phe Asp Ile
            565                 570                 575
```

-continued

```
Gly Ile Asp Thr Asp Gly Phe Ser Phe Val Gly Val Ser Asn Leu Pro
            580                 585                 590
Lys Leu Glu Phe Pro Leu Ser Ala Pro Tyr Met Gly Ile Gln Leu Ala
        595                 600                 605
Lys Val Arg Leu Ala Ser Asn Ile Arg Ser Ser Met Thr Lys Leu
    610                 615                 620

<210> SEQ ID NO 3
<211> LENGTH: 1926
<212> TYPE: DNA
<213> ORGANISM: Feline calicivirus
<400> SEQUENCE: 3
atggaatttg gaactgtttg ggactgtaac cagtcaccat tggaaattta tctagagtcc     60
atccttggag atgatgaatg ggcctccact tatgatgcaa ttgaccccgc agttccacca    120
atgcactggg atgatgctgg aaagattttc cagccacacc ctggtgtgct gatgcaccac    180
ctcattgcaa aggttgctga ggcttgggat ccagatctac ctctctttcg tttggagggt    240
gatgatggat caatcacaac acctgagcag ggaacaatgg ttggtggggt aattgctgaa    300
cccagcgctc aaatgtcggc agctgccgac atggccacag ggaagagcgt tgactctgag    360
tgggaagctt tcttctcctt tcacaccagc gtcaactgga gcacatctga aactcaagga    420
aagattctct ttaaacaatc tttaggaccc ttactcaatc cctatctttc tcatctcgca    480
aaactctatg tcgcttggtc tggttctgtt gaggtaagat tttctatttc cggatctggc    540
gtgttcgggg ggaaattggc tgctattgtt gtgccaccag gcattgaacc tgttcaaagc    600
acatcaatgc ttcaataccc gcatgttctc ttcgacgctc gccaggttga gcctgtcatc    660
tttgctattc ctgatttaag gagcaatcta tatcacctaa tgtccgacac tgacactaca    720
tcccttgtaa ttatggtgta taatgatctt atcaaccctt atgctaatga cacaaactct    780
tctggctgta tcgtcactgt tgagacaaaa cctggtcctg atttcaagtt tcacctctta    840
aaaccacctg gatctatgct aacacatggg tcagtacctt ctgatctaat ccctaaatca    900
tcttctctct ggattggtaa tcgccattgg tctgacatta ctgatttcat catacgtcct    960
tttgtctttc aagcgaatcg acactttgac tttaaccagg aaactgctgg gtggagtacg   1020
ccgagattcc gaccaataac catcacagtt agtgagagca acatgtcaaa actcggaata   1080
ggtgttgcaa ctgactacat tgtccctggg atcccggacg gctggcctga cacaacaatc   1140
ccagagcagc tcacccctgc aggtatatac tcaatcacag caagtaatgg cactgacatc   1200
accacggccg caggctatga tgctgcagaa acaatcgtaa acacaacaaa cttcaaaagc   1260
atgtacattt gtgggtcatt gcaaagagcc tggggtgata agaaaatctc aaacactgct   1320
tttataacca cagcagtcag aaaaggtaac tcgatcgagc catcaaacac aattgacatg   1380
acaaagcttg tcgtgtacca ggatgcacat gtgggtgaag aggtccaaac ctccgacatc   1440
actcttgcac ttcttggtta cacgggaatt ggtgaagaag caattggttc agacagagat   1500
aaagtggtgc ggatcagtgt ccttccagaa actggtgccc gtggtggtaa tcaccctatc   1560
ttttataaaa attcgattaa attgggttat gtgattaggt caattgatgt gtttaactct   1620
cagattctgc acacctcaag gcagctatcc ttaaacaact atctactccc tccagattct   1680
tttgcagtct atagaatact tgactctaat ggttcatggt ttgatattgg tattgatact   1740
gatggctttt cttttgttgg tgtatctaac ttacctaaac tagagtttcc tctttctgcc   1800
tcctacatgg gaattcagct ggctaaggtt cgccttgcct ctaacattag gagtagtatg   1860
```

```
actaaattat gaattcaata ttgggcttaa ttgatactgt tacaaacact attggtaaag    1920
ctcagc                                                               1926
```

<210> SEQ ID NO 4
<211> LENGTH: 623
<212> TYPE: PRT
<213> ORGANISM: Feline calicivirus

<400> SEQUENCE: 4

```
Met Glu Phe Gly Thr Val Trp Asp Cys Asn Gln Ser Pro Leu Glu Ile
  1               5                  10                  15

Tyr Leu Glu Ser Ile Leu Gly Asp Asp Glu Trp Ala Ser Thr Tyr Asp
                 20                  25                  30

Ala Ile Asp Pro Ala Val Pro Pro Met His Trp Asp Asp Ala Gly Lys
             35                  40                  45

Ile Phe Gln Pro His Pro Gly Val Leu Met His His Leu Ile Ala Lys
         50                  55                  60

Val Ala Glu Ala Trp Asp Pro Asp Leu Pro Leu Phe Arg Leu Glu Gly
 65                  70                  75                  80

Asp Asp Gly Ser Ile Thr Thr Pro Glu Gln Gly Thr Met Val Gly Gly
                 85                  90                  95

Val Ile Ala Glu Pro Ser Ala Gln Met Ser Ala Ala Asp Met Ala
            100                 105                 110

Thr Gly Lys Ser Val Asp Ser Glu Trp Glu Ala Phe Phe Ser Phe His
            115                 120                 125

Thr Ser Val Asn Trp Ser Thr Ser Glu Thr Gln Gly Lys Ile Leu Phe
        130                 135                 140

Lys Gln Ser Leu Gly Pro Leu Leu Asn Pro Tyr Leu Ser His Leu Ala
145                 150                 155                 160

Lys Leu Tyr Val Ala Trp Ser Gly Ser Val Glu Val Arg Phe Ser Ile
                165                 170                 175

Ser Gly Ser Gly Val Phe Gly Gly Lys Leu Ala Ala Ile Val Val Pro
            180                 185                 190

Pro Gly Ile Glu Pro Val Gln Ser Thr Ser Met Leu Gln Tyr Pro His
        195                 200                 205

Val Leu Phe Asp Ala Arg Gln Val Glu Pro Val Ile Phe Ala Ile Pro
    210                 215                 220

Asp Leu Arg Ser Asn Leu Tyr His Leu Met Ser Asp Thr Asp Thr Thr
225                 230                 235                 240

Ser Leu Val Ile Met Val Tyr Asn Asp Leu Ile Asn Pro Tyr Ala Asn
                245                 250                 255

Asp Thr Asn Ser Ser Gly Cys Ile Val Thr Val Glu Thr Lys Pro Gly
            260                 265                 270

Pro Asp Phe Lys Phe His Leu Leu Lys Pro Pro Gly Ser Met Leu Thr
        275                 280                 285

His Gly Ser Val Pro Ser Asp Leu Ile Pro Lys Ser Ser Ser Leu Trp
    290                 295                 300

Ile Gly Asn Arg His Trp Ser Asp Ile Thr Asp Phe Ile Ile Arg Pro
305                 310                 315                 320

Phe Val Phe Gln Ala Asn Arg His Phe Asp Phe Asn Gln Glu Thr Ala
                325                 330                 335

Gly Trp Ser Thr Pro Arg Phe Arg Pro Ile Thr Ile Thr Val Ser Glu
            340                 345                 350

Ser Asn Met Ser Lys Leu Gly Ile Gly Val Ala Thr Asp Tyr Ile Val
```

-continued

```
                355                 360                 365
        Pro Gly Ile Pro Asp Gly Trp Pro Asp Thr Thr Ile Pro Glu Gln Leu
            370                 375                 380
Thr Pro Ala Gly Ile Tyr Ser Ile Thr Ala Ser Asn Gly Thr Asp Ile
385                 390                 395                 400
Thr Thr Ala Ala Gly Tyr Asp Ala Ala Glu Thr Ile Val Asn Thr Thr
                405                 410                 415
Asn Phe Lys Ser Met Tyr Ile Cys Gly Ser Leu Gln Arg Ala Trp Gly
            420                 425                 430
Asp Lys Lys Ile Ser Asn Thr Ala Phe Ile Thr Thr Ala Val Arg Lys
                435                 440                 445
Gly Asn Ser Ile Glu Pro Ser Asn Thr Ile Asp Met Thr Lys Leu Val
    450                 455                 460
Val Tyr Gln Asp Ala His Val Gly Glu Glu Val Gln Thr Ser Asp Ile
465                 470                 475                 480
Thr Leu Ala Leu Leu Gly Tyr Thr Gly Ile Gly Glu Glu Ala Ile Gly
                485                 490                 495
Ser Asp Arg Asp Lys Val Val Arg Ile Ser Val Leu Pro Glu Thr Gly
            500                 505                 510
Ala Arg Gly Gly Asn His Pro Ile Phe Tyr Lys Asn Ser Ile Lys Leu
            515                 520                 525
Gly Tyr Val Ile Arg Ser Ile Asp Val Phe Asn Ser Gln Ile Leu His
    530                 535                 540
Thr Ser Arg Gln Leu Ser Leu Asn Asn Tyr Leu Leu Pro Pro Asp Ser
545                 550                 555                 560
Phe Ala Val Tyr Arg Ile Leu Asp Ser Asn Gly Ser Trp Phe Asp Ile
                565                 570                 575
Gly Ile Asp Thr Asp Gly Phe Ser Phe Val Gly Val Ser Asn Leu Pro
            580                 585                 590
Lys Leu Glu Phe Pro Leu Ser Ala Ser Tyr Met Gly Ile Gln Leu Ala
            595                 600                 605
Lys Val Arg Leu Ala Ser Asn Ile Arg Ser Ser Met Thr Lys Leu
    610                 615                 620
```

<210> SEQ ID NO 5
<211> LENGTH: 1926
<212> TYPE: DNA
<213> ORGANISM: Feline calicivirus

<400> SEQUENCE: 5

| | | | |
|---|---|---|---|
| atggaatttg gaactgtttg ggactgtaac cagtcaccat ggaaattta tctagagtcc | 60 |
| atccttggag atgatgaatg ggcctccact tatgatgcaa ttgaccccgc agttccacca | 120 |
| atgcactggg atgatgctgg aaagattttc cagccacacc tggtgtgct gatgcaccac | 180 |
| ctcattgcaa aggttgctga ggcttgggat ccagatctac ctctctttcg tttggagggt | 240 |
| gatgatggat caatcacaac acctgagcag gaacaatgg ttggtggggt aattgctgaa | 300 |
| cccagcgctc aaatgtcggc agctgccgac atggccacag gaagagcgt tgactctgag | 360 |
| tgggaagctt tcttctcctt tcacaccagc gtcaactgga gcacatctga aactcaagga | 420 |
| aagattctct ttaaacaatc tttaggaccc ttactcaatc cctatctttc tcatctcgca | 480 |
| aaactctatg tcgcttttgc tggttctgtt gaggtaagat tttctatttc cggatctggc | 540 |
| gtgttcgggg ggaaattggc tgctattgtt gtgccaccag gcattgaacc tgttcaaagc | 600 |
| acatcaatgc ttcaataccc gcatgttctc ttcgacgctc gccaggttga gctgtcatc | 660 |

-continued

```
tttgctattc ctgatttaag gagcaatcta tatcacctaa tgtccgacac tgacactaca     720
tcccttgtaa ttatggtgta taatgatctt atcaaccctt atgctaatga cacaaactct     780
tctggctgta tcgtcactgt tgagacaaaa cctggtcctg atttcaagtt tcacctctta     840
aaaccacctg gatctatgct aacacatggg tcagtacctt ctgatctaat ccctaaatca     900
tcttctctct ggattggtaa tcgccattgg tctgacatta ctgatttcat catacgtcct     960
tttgtctttc aagcgaatcg acactttgac tttaaccagg aaactgctgg gtggagtacg    1020
ccgagattcc gaccaataac catcacagtt agtgagagca acatgtcaaa actcggaata    1080
ggtgttgcaa ctgactacat tgtccctggg atcccggacg gctggcctga cacaacaatc    1140
ccagagcagc tcacccctgc aggtatatac tcaatcacag caagtaatgg cacagacatc    1200
accacggccg caggctatga tgctgcagaa acaatcgtaa acacaacaaa cttcaaaagc    1260
atgtacattt gtgggtcatt gcaaagagcc tgggatgata agaaaatctc aaacactgct    1320
tttataacca cagcagtcag aaaaggtaac tcgatcgagc catcaaacac aattgacatg    1380
acaaagcttg tcgtgtacca ggatgcacat gtgggtgaag aagtccaaac ctccgacatc    1440
actcttgcac ttcttggtta cacgggaatt ggtgaagaag caattggttc agacagagat    1500
aaagtggtgc ggatcagtgt ccttggagaa actggtgccc gtggtggtaa tcaccctatc    1560
ttttataaaa attcgattaa attgggttat gtgattaggt caattgatgt gtttaactct    1620
cagattctgc actcctcaag gcagctatcc ttaaacaact atctactccc tccagattct    1680
tttgcagtct atagaatact tgactctaat ggttcatggt ttgatattgg tattgatact    1740
gagtttcctg atggcttttc ttttgttggt gtatctaact tacctaaact actttctgcc    1800
tcctactagg gaattcagct ggctaaggtt cgccttgcct ctaacattag gagtagtatg    1860
actaaattat gaattcaata ttgggcttaa ttgatactgt tacaaacact attggtaaag    1920
ctcagc                                                               1926
```

```

<210> SEQ ID NO 6
<211> LENGTH: 622
<212> TYPE: PRT
<213> ORGANISM: Feline calicivirus

<400> SEQUENCE: 6

Met Glu Phe Gly Thr Val Trp Asp Cys Asn Gln Ser Pro Leu Glu Ile
  1               5                  10                  15

Tyr Leu Glu Ser Ile Leu Gly Asp Asp Glu Trp Ala Ser Thr Tyr Asp
             20                  25                  30

Ala Ile Asp Pro Ala Val Pro Pro Met His Trp Asp Asp Ala Gly Lys
         35                  40                  45

Ile Phe Gln Pro His Pro Gly Val Leu Met His His Leu Ile Ala Lys
     50                  55                  60

Val Ala Glu Ala Trp Asp Pro Asp Leu Pro Leu Phe Arg Leu Glu Gly
 65                  70                  75                  80

Asp Asp Gly Ser Ile Thr Thr Pro Glu Gln Gly Thr Met Val Gly Gly
                 85                  90                  95

Val Ile Ala Glu Pro Ser Ala Gln Met Ser Ala Ala Ala Asp Met Ala
            100                 105                 110

Thr Gly Lys Ser Val Asp Ser Glu Trp Glu Ala Phe Phe Ser Phe His
        115                 120                 125

Thr Ser Val Asn Trp Ser Thr Ser Glu Thr Gln Gly Lys Ile Leu Phe
    130                 135                 140
```

-continued

```
Lys Gln Ser Leu Gly Pro Leu Leu Asn Pro Tyr Leu Ser His Leu Ala
145                 150                 155                 160

Lys Leu Tyr Val Ala Leu Ala Gly Ser Val Glu Val Arg Phe Ser Ile
                165                 170                 175

Ser Gly Ser Gly Val Phe Gly Gly Lys Leu Ala Ala Ile Val Val Pro
            180                 185                 190

Pro Gly Ile Glu Pro Val Gln Ser Thr Ser Met Leu Gln Tyr Pro His
        195                 200                 205

Val Leu Phe Asp Ala Arg Gln Val Glu Pro Val Ile Phe Ala Ile Pro
    210                 215                 220

Asp Leu Arg Ser Asn Leu Tyr His Leu Met Ser Asp Thr Asp Thr Thr
225                 230                 235                 240

Ser Leu Val Ile Met Val Tyr Asn Asp Leu Ile Asn Pro Tyr Ala Asn
                245                 250                 255

Asp Thr Asn Ser Ser Gly Cys Ile Val Thr Val Glu Thr Lys Pro Gly
            260                 265                 270

Pro Asp Phe Lys Phe His Leu Leu Lys Pro Pro Gly Ser Met Leu Thr
        275                 280                 285

His Gly Ser Val Pro Ser Asp Leu Ile Pro Lys Ser Ser Ser Leu Trp
    290                 295                 300

Ile Gly Asn Arg His Trp Ser Asp Ile Thr Asp Phe Ile Ile Arg Pro
305                 310                 315                 320

Phe Val Phe Gln Ala Asn Arg His Phe Asp Phe Asn Gln Glu Thr Ala
                325                 330                 335

Gly Trp Ser Thr Pro Arg Phe Arg Pro Ile Thr Ile Thr Val Ser Glu
            340                 345                 350

Ser Asn Met Ser Lys Leu Gly Ile Gly Val Ala Thr Asp Tyr Ile Val
        355                 360                 365

Pro Gly Ile Pro Asp Gly Trp Pro Asp Thr Thr Ile Pro Glu Gln Leu
    370                 375                 380

Thr Pro Ala Gly Ile Tyr Ser Ile Thr Ala Ser Asn Gly Thr Asp Ile
385                 390                 395                 400

Thr Thr Ala Ala Gly Tyr Asp Ala Ala Glu Thr Ile Val Asn Thr Thr
                405                 410                 415

Asn Phe Lys Ser Met Tyr Ile Cys Gly Ser Leu Gln Arg Ala Trp Asp
            420                 425                 430

Asp Lys Lys Ile Ser Asn Thr Ala Phe Ile Thr Ala Val Arg Lys
        435                 440                 445

Gly Asn Ser Ile Glu Pro Ser Asn Thr Ile Asp Met Thr Lys Leu Val
    450                 455                 460

Val Tyr Gln Asp Ala His Val Gly Glu Glu Val Gln Thr Ser Asp Ile
465                 470                 475                 480

Thr Leu Ala Leu Leu Gly Tyr Thr Gly Ile Gly Glu Glu Ala Ile Gly
                485                 490                 495

Ser Asp Arg Asp Lys Val Val Arg Ile Ser Val Leu Gly Glu Thr Gly
            500                 505                 510

Ala Arg Gly Gly Asn His Pro Ile Phe Tyr Lys Asn Ser Ile Lys Leu
        515                 520                 525

Gly Tyr Val Ile Arg Ser Ile Asp Val Phe Asn Ser Gln Ile Leu His
    530                 535                 540

Ser Ser Arg Gln Leu Ser Leu Asn Asn Tyr Leu Leu Pro Pro Asp Ser
545                 550                 555                 560
```

```
Phe Ala Val Tyr Arg Ile Leu Asp Ser Asn Gly Ser Trp Phe Asp Ile
                565                 570                 575

Gly Ile Asp Thr Glu Phe Pro Asp Gly Phe Ser Phe Val Gly Val Ser
            580                 585                 590

Asn Leu Pro Lys Leu Leu Ser Ala Ser Tyr Gly Ile Gln Leu Ala Lys
            595                 600                 605

Val Arg Leu Ala Ser Asn Ile Arg Ser Ser Met Thr Lys Leu
    610                 615                 620

<210> SEQ ID NO 7
<211> LENGTH: 626
<212> TYPE: PRT
<213> ORGANISM: Feline calicivirus

<400> SEQUENCE: 7

Pro Glu Phe Gly Thr Val Trp Asp Cys Asn Arg Ser Pro Leu Glu Ile
 1               5                  10                  15

Tyr Leu Glu Ser Ile Leu Gly Asp Asp Glu Trp Ala Ser Thr Phe Asp
             20                  25                  30

Ala Val Asp Pro Val Val Pro Met His Trp Gly Ala Ala Gly Lys
         35                  40                  45

Ile Phe Gln Pro His Pro Gly Val Leu Met His His Leu Ile Gly Lys
     50                  55                  60

Val Ala Ala Gly Trp Asp Pro Asp Leu Pro Leu Ile Arg Leu Glu Ala
 65                  70                  75                  80

Asp Asp Gly Ser Ile Thr Ala Pro Glu Gln Gly Thr Met Val Gly Gly
                 85                  90                  95

Val Ile Ala Glu Pro Ser Ala Gln Met Ser Thr Ala Ala Asp Met Ala
            100                 105                 110

Thr Gly Lys Ser Val Asp Ser Glu Trp Glu Ala Phe Phe Ser Phe His
        115                 120                 125

Thr Ser Val Asn Trp Ser Thr Ser Glu Thr Gln Gly Lys Ile Leu Phe
    130                 135                 140

Lys Gln Ser Leu Gly Pro Leu Leu Asn Pro Tyr Leu Ser His Leu Ala
145                 150                 155                 160

Lys Leu Tyr Val Ala Trp Ser Gly Ser Ile Glu Val Arg Phe Ser Ile
                165                 170                 175

Ser Gly Ser Gly Val Phe Gly Gly Lys Leu Ala Ala Ile Val Val Pro
            180                 185                 190

Pro Gly Val Asp Pro Val Gln Ser Thr Ser Met Leu Gln Tyr Pro His
        195                 200                 205

Val Leu Phe Asp Ala Arg Gln Val Glu Pro Val Ile Phe Cys Leu Pro
    210                 215                 220

Asp Leu Arg Ser Thr Leu Tyr His Leu Met Ser Asp Thr Asp Thr Thr
225                 230                 235                 240

Ser Leu Val Ile Met Val Tyr Asn Asp Leu Ile Asn Pro Tyr Ala Asn
                245                 250                 255

Asp Thr Asn Ser Ser Gly Cys Ile Val Thr Val Glu Thr Lys Pro Gly
            260                 265                 270

Pro Asp Phe Lys Phe His Leu Leu Lys Pro Pro Gly Ser Met Leu Thr
        275                 280                 285

His Gly Ser Val Pro Ser Asp Leu Ile Pro Lys Ser Ser Ser Leu Trp
    290                 295                 300

Ile Gly Asn Arg His Trp Ser Asp Ile Thr Asp Phe Ile Ile Arg Pro
305                 310                 315                 320
```

```
Phe Val Phe Gln Ala Asn Arg His Phe Asp Phe Asn Gln Glu Thr Ala
                325                 330                 335
Gly Trp Ser Thr Pro Arg Phe Arg Pro Ile Ser Val Thr Ile Thr Glu
            340                 345                 350
Gln Asn Gly Ala Lys Leu Gly Ile Gly Val Ala Thr Asp Tyr Ile Val
        355                 360                 365
Pro Gly Ile Pro Asp Gly Trp Pro Asp Thr Thr Ile Pro Gly Glu Leu
    370                 375                 380
Ile Pro Ala Gly Asp Tyr Ala Ile Thr Asn Gly Thr Gly Asn Asp Ile
385                 390                 395                 400
Thr Thr Ala Thr Gly Tyr Asp Thr Ala Asp Ile Ile Lys Asn Asn Thr
                405                 410                 415
Asn Phe Arg Gly Met Tyr Ile Cys Gly Ser Leu Gln Arg Ala Trp Gly
            420                 425                 430
Asp Lys Lys Ile Ser Asn Thr Ala Phe Ile Thr Thr Ala Thr Leu Asp
        435                 440                 445
Gly Asp Asn Asn Asn Lys Ile Asn Pro Cys Asn Thr Ile Asp Gln Ser
    450                 455                 460
Lys Ile Val Val Phe Gln Asp Ala His Val Gly Lys Lys Ala Gln Thr
465                 470                 475                 480
Ser Asp Asp Thr Leu Ala Leu Leu Gly Tyr Thr Gly Ile Gly Glu Gln
                485                 490                 495
Ala Ile Gly Ser Asp Arg Asp Arg Val Val Arg Ile Ser Thr Leu Pro
            500                 505                 510
Glu Thr Gly Ala Arg Gly Gly Asn His Pro Ile Phe Tyr Lys Asn Ser
        515                 520                 525
Ile Lys Leu Gly Tyr Val Ile Arg Ser Ile Asp Val Phe Asn Ser Gln
    530                 535                 540
Ile Leu His Thr Ser Arg Gln Leu Ser Leu Asn His Tyr Leu Leu Pro
545                 550                 555                 560
Pro Asp Ser Phe Ala Val Tyr Arg Ile Ile Asp Ser Asn Gly Ser Trp
                565                 570                 575
Phe Asp Ile Gly Ile Asp Ser Asp Gly Phe Ser Phe Val Gly Val Ser
            580                 585                 590
Gly Phe Gly Lys Leu Glu Phe Pro Leu Ser Ala Ser Tyr Met Gly Ile
        595                 600                 605
Gln Leu Ala Lys Ile Arg Leu Ala Ser Asn Ile Arg Ser Pro Met Thr
    610                 615                 620
Lys Leu
625

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: upstream
      primer for capsid antigen

<400> SEQUENCE: 8
atggaatttg gaactgtttg gg                                              22

<210> SEQ ID NO 9
<211> LENGTH: 20
<212> TYPE: DNA
<213> ORGANISM: Artificial Sequence
```

```
<220> FEATURE:
<223> OTHER INFORMATION: Description of Artificial Sequence: downstream
      primer for capsid antigen

<400> SEQUENCE: 9
gctgagcttt accaatagtg                                              20
```